US 10,791,957 B1

(12) United States Patent
Damadian

(10) Patent No.: US 10,791,957 B1
(45) Date of Patent: Oct. 6, 2020

(54) MAGNETIC RESONANCE IMAGING

(75) Inventor: Raymond V. Damadian, Woodbury, NY (US)

(73) Assignee: FONAR Corporation, Melville, NY (US)

( * ) Notice: Subject to any disclaimer, the term of this patent is extended or adjusted under 35 U.S.C. 154(b) by 1672 days.

(21) Appl. No.: 11/558,436

(22) Filed: Nov. 9, 2006

(51) Int. Cl.
*A61B 5/055* (2006.01)
*G01R 33/38* (2006.01)
*G01R 33/28* (2006.01)

(52) U.S. Cl.
CPC ............ *A61B 5/055* (2013.01); *G01R 33/28* (2013.01); *G01R 33/3806* (2013.01)

(58) Field of Classification Search
CPC ...... G01R 33/28; G01R 33/3806; A61B 5/055
USPC ........ 600/410, 420, 411, 415; 324/307, 309, 324/318, 322
See application file for complete search history.

(56) References Cited

U.S. PATENT DOCUMENTS

| | | |
|---|---|---|
| 4,766,378 A | 8/1988 | Danby et al. |
| 5,061,897 A | 10/1991 | Danby et al. |
| 5,106,897 A | 4/1992 | Chen et al. |
| 5,124,651 A | 6/1992 | Danby et al. |
| 5,590,654 A * | 1/1997 | Prince ........................... 600/420 |
| 5,592,089 A | 1/1997 | Danby et al. |
| 5,647,361 A | 7/1997 | Damadian et al. |
| 6,061,587 A | 5/2000 | Kucharczyk et al. |
| 6,201,394 B1 | 3/2001 | Danby et al. |
| 6,208,145 B1 * | 3/2001 | Denby et al. ................. 324/319 |
| 6,225,805 B1 | 5/2001 | Damadian et al. |
| 6,272,370 B1 | 8/2001 | Gillies et al. |
| 6,335,623 B1 * | 1/2002 | Damadian et al. ........... 324/320 |
| 6,400,157 B1 * | 6/2002 | Bonanni ................. G01R 33/54 324/309 |
| 6,541,973 B1 * | 4/2003 | Denby et al. ................. 324/318 |
| 6,549,800 B1 | 4/2003 | Atalar et al. |
| 6,828,792 B1 | 12/2004 | Danby et al. |
| 6,954,069 B2 | 10/2005 | Harvey et al. |
| 2001/0039378 A1 | 11/2001 | Lampman et al. |
| 2002/0123681 A1 * | 9/2002 | Zuk et al. ...................... 600/410 |
| 2003/0109849 A1 | 6/2003 | Hammer et al. |
| 2003/0174036 A1 * | 9/2003 | Wang et al. ................... 335/299 |
| 2004/0039277 A1 * | 2/2004 | Watanbe ................ A61B 5/055 600/410 |
| 2004/0242993 A1 * | 12/2004 | Tajima ......................... 600/417 |

(Continued)

*Primary Examiner* — Mark D Remaly
(74) *Attorney, Agent, or Firm* — Raymond Van Dyke; Van Dyke Law

(57) ABSTRACT

An open MRI methodology and system that allows dynamic viewing and access to a patient. In intraoperative MRI, the MRI apparatus is configured in the shape of a typical operating room, with full 360° access to the patient. The MRI apparatus encompasses the entire operating room with magnets located on or near the ceiling and floor of the operating room. The remainder of the MRI apparatus, including the control computer, and imaging monitor, may be located outside of the MRI operating room, in order to keep the operating room free of unnecessary equipment, or located inside of the MRI operating room, as desired for operability of the MRI. The patient is placed over the magnet in the floor, the only fixed location in the operating room. The operating room may contain typical operating equipment, as needed, such as cardiopulmonary bypass units, surgical navigation systems, endoscopy systems, and anesthesia carts.

48 Claims, 20 Drawing Sheets

(56) References Cited

U.S. PATENT DOCUMENTS

2005/0054910 A1    3/2005  Tremblay et al.
2005/0080333 A1    4/2005  Piron et al.
2007/0222450 A1*  9/2007  Green et al. ................. 324/318

* cited by examiner

MAGNETIC RESONANCE IMAGING

FIELD OF THE INVENTION

The present invention relates to improvements in the use of magnetic resonance imaging, and, more particularly, to improvements in surgical and treatment methodologies due to an improved structure of a magnetic resonance imaging device and operational techniques in the usage thereof.

BACKGROUND OF THE INVENTION

The capability and utility of imaging the internal anatomical structures of living organisms using nuclear magnetic resonance imaging signals is well established. Magnetic Resonance Imaging ("MRI"), also known previously as Nuclear Magnetic Resonance ("NMR"), is highly sensitive to the relaxation times of atomic nuclei emitting a magnetic resonance imaging signal, and different relaxation times are manifested as different contrasts within an image. Indeed, different tissues within the organs and structures of an organism exhibit markedly different relaxation times.

As conceptualized and discovered just over thirty years ago by Dr. Raymond V. Damadian, Applicant herein, diseased and injured tissues have a different magnetic resonance signature than healthy tissue, i.e., diseased and damaged tissues have different atomic relaxation times than equivalent healthy tissues and can be distinguished therefrom in vivo. By virtue of Dr. Damadian's discoveries, MRI provides a potent diagnostic and therapeutic tool for the detection and treatment of injured and diseased tissues within patients.

In MRI diagnostics, a body is subjected to a constant main magnetic field. Another magnetic field, in the form of electromagnetic radio frequency ("RF") pulses, is applied orthogonally to the constant main magnetic field. As is well known to those of skill in the art, the RF pulses employed have a particular frequency and shape that are chosen to affect particular nuclei, typically hydrogen, present in sufficient quantities in the body. The RF pulses excite the nuclei, increasing the energy state of the nuclei. After the pulse has terminated, however, the nuclei thereafter relax and release RF emissions in a manner corresponding to the respective RF pulses, which are measured and processed into images for display. As discussed, diseased and/or damaged tissues are thereby imaged. With advances in computational power and algorithmic design, the collection, processing and display of the images are better facilitated, making use of the information more dynamic and real time.

A conventional system for utilizing MRI technology for treating patients is shown in FIGS. 1A and 1B of the Drawings. The system, designated generally by the reference numeral 100, includes a tube-shaped MRI apparatus, designated generally by the reference number 110, which is generally comprised of a magnet that provides a magnetic flux path for magnetic flux, as is understood in the art. The tube-shaped MRI apparatus accepts a table 115, in a horizontal motion through an opening or gap 120. A patient or organism, designated generally by the reference numeral 105, is positioned on the table 115 within the gap 120 so that MRI data may be acquired about at least a portion of said patient 105.

For many early years in the development of MRI technology, the gap 120 (exaggerated in the FIGURE) was fairly small due to the technological limitations of the system 100, e.g., generation of sufficient field strength across said gap 120. A typical configuration of the earlier systems 100 is the well-known tube formation, into which the patient 105 is inserted and positioned, whereby tight constriction of the patient 105 was needed to fit within the narrow gap 120 size. As a result of magnetic resonance data acquisition in such systems, surgeries and other medical procedures could be mapped-out or otherwise planned in advance. Having reviewed and studied the visual data obtained from MRI imaging of issues of interest, surgeons could then perform minimally-invasive procedures on patients, i.e., the internal data acquired helps the surgeon prepare for the subsequent surgery or treatment. An example of a technique that makes sophisticated use of MRI for surgeries is set forth in Applicant's U.S. Pat. No. 5,647,361, incorporated herein by reference, in which MRI data acquisition is employed to ascertain a pathway for instrument insertion and other mechanisms to facilitate surgery and other treatment.

In typical MRI systems, a display or monitor allows the technician, surgeon or other medical professional to envision the interior surfaces under scan and better facilitate treatment, e.g., focus the image on particular tissues of interest, including cancers, tumors, diseased tissues, tissues bordering diseased tissues, etc., pre-operatively providing information on how best to subsequently treat those tissues. The display is connected to a computer and an input/output (I/O) interface, as is understood in the art. Computation for the images from the raw data, including Fast Fourier Transformations (FFTs), can be performed by the computer or by another connected thereto, e.g., over the Internet or other telecommunications linkage. Specialized chipsets or other computational accelerants, e.g., graphics or processing units, cam be employed to speed-up the calculations, as is well known to those skilled in the art. An improvement to the interface is set forth in Applicant's Assignee's U.S. Pat. Nos. 6,801,037 and 7,081,750, incorporated herein by reference.

Although a revolutionary technology, the usage of MRI systems has nonetheless suffered from some serious drawbacks in practical usage in the years since Dr. Damadian first investigated this technology. A chief problem with tubular configurations is claustrophobia, mostly the result of the aforementioned limitations imposed by the physics of the devices. It should be apparent that the configuration shown in FIGS. 1A and 1B offers a much larger space than early devices. Although the service performed is quite beneficial, most patients nonetheless fear tube-configuration MRI devices, some quite seriously. Furthermore, since MRI data acquisition took considerable time, almost all patients enclosed in the tube become uncomfortable or annoyed.

Additionally, the tight and closed nature of these device configurations severely limits their dynamic usage in treatment. For example, patients are first sent to get an MRI, and the results are analyzed as a starting point for future treatment, such as surgery. Similarly, post-operative MRI data is employed to review the surgical results. Much like getting an X-ray, the MRI data is not dynamically or intraoperatively available to the surgeon or other immediate medical practitioner, making the MRI data of some interest diagnostically but of limited use in treatment.

To overcome these and additional drawbacks of these "first generation" systems, limited primarily by the physics of the configuration, Dr. Damadian developed a more practical system that shed some of the bounds of the more primitive and traditional first generation MRI systems exemplified by the device shown in FIGS. 1A and 1B.

With reference now to FIGS. 2A and 2B of the Drawings, there is shown an exemplary MRI device in the so-called second generation system. Instead of an enclosure or tube for tightly housing the patient therein, these second generation-systems are generally referred to as "open MRI systems." In an open MRI, designated generally by the reference numeral 200, a magnet structure 210 includes a pair of vertically-extending sidewalls 212 and an upper flux return source, including a pair of flux return members 214 and 216, respectively, extending between the aforementioned sidewalls 212. A lower flux return source structure includes a similar pair of flux return members 224 and 226, respectively. With particular reference to FIG. 2B, a pair of round and generally cylindrical ferromagnetic poles 225 project inwardly from the opposed sidewalls 212 along a magnetic axis or pole axis 230, as shown in FIG. 2A, forming a pair of opposed pole surfaces 235 and 240, respectively, defining a gap, generally designated by the reference numeral 220, therebetween through which magnetic flux flows. A patient or organism, designated generally by the reference number 205, as shown in cross-sectional viewpoint in FIG. 2A, is positioned within this gap 220 to acquire MRI data about at least a portion of said patient 205. A flux source, e.g., coils 245, as shown in FIG. 2B, may be resistive or super-conducting coils surrounding the poles or may be permanent magnetic material, as is understood in the art.

A more detailed description of this second generation open MRI system is set forth in Applicant's U.S. Pat. No. 6,828,792, which is incorporated by reference herein.

These second generation or "open MRI" devices have opened up a range of practicalities over the more limited first generation systems exemplified in FIGS. 1A and 1B and accompanying text. For the consumer, there are no more small, horizontally-arranged tubes to be inserted into and claustrophobically confined. For the diagnostician, patients can be placed in a variety of positions other than prone, e.g., standing or load-bearing positions become available, making MRI data of body parts in action possible. As shown in FIG. 2A, a patient is being imaged substantially vertically, showing the knee or hip or other body part under the influence of gravity. The full measure of advantages of these devices is still being determined, and a variety of open MRI designs are on the market. A more detailed description of the diagnostic and therapeutic advantages of open MRI systems can be found in Applicant's U.S. Pat. No. 6,828,792, discussed hereinabove.

Although far more practical than closed systems, the open systems, too, have drawbacks, and the present invention is directed to ushering in another generation of MRI devices that offer new capabilities over the old.

One of the continuing problems of the present art is patient accessibility by the surgeon or diagnostician. Indeed, the openness of an open MRI is almost entirely from the perspective of the patient. Surgeons, diagnosticians and the like have had no dynamic patient access in tube systems and only limited access to the patient in open systems. Further, as with taking an X-ray, magnetic resonance imaging is something currently prescribed, administered and reviewed subsequently. Although open systems have greatly increased the functionality of MR technology, dynamic intraoperative usage of the imaging in patient treatment is the Holy Grail in medicine.

Further efforts to increase the usefulness and aesthetics of MRI treatment have expanded upon the concept of open MRI and also improved on aspects of patient access. For example, Applicant herein is a named inventor in U.S. Pat. Nos. 6,201,394, 6,208,145 and 6,225,805 in which various improvements have been made in MR imaging technology. In particular, each patent addresses the same problems of the first and second generation systems: the problems of claustrophobia, access to the patient during a procedure and making better use of MRI data during a procedure. In many respects, these patents solve aspects of the perennial problems of confinement and dynamic usage of the data.

Although these approaches are significant advancements over the prior generational innovations, further advancements have recently been made to better facilitate the patient experience, overcome the problems of patient access and functionality, and otherwise improve the usefulness of MRI data to the physician, surgeon or other practitioner dynamically employing the data for the patient's gain.

SUMMARY OF THE INVENTION

The present invention is an entirely open MRI methodology and system that allows a surgeon or other treatment provider dynamic viewing and intraoperative access to a patient being imaged. With the intraoperative MRI methodologies of the present invention, the MRI apparatus is configured in the shape of a typical operating room, with 360° access to the patient.

In a preferred embodiment, the MRI apparatus encompasses the entire operating room with magnets located on or near the ceiling and floor of the operating room. The remainder of the MRI apparatus, including the shielding, control computer and imaging monitor may be located outside of the MRI operating room, in order to keep the operating room free of unnecessary equipment, or located inside of the MRI operating room, as desired for accessibility and operability of the MRI. The patient is placed over the magnet in the floor, the only fixed location in the operating room. The operating room may contain typical operating equipment, as needed, including such equipment as respirometers, heart pumps, cardiopulmonary bypass units, lithotriptors, surgical navigation systems, endoscopy systems, anesthesia carts, arthroscopy units, defibrillators, thermal regulation systems, fiberoptic lighting systems, and electrophysiology platforms such as electroencephalogram (EEG), electrocardiogram (EKG), and electromyogram (EMG) systems, as well as other attendant instrumentation.

In a preferred embodiment, the MRI apparatus, including the magnets in the ceiling and floor of the MRI operating room, are sized to accommodate large areas of interest, such as the entire body or system. In another preferred embodiment, the MRI apparatus, including the magnets in the ceiling and floor of the MRI operating room, are sized to accommodate small areas of interest, such as a limb, organ, or tissue.

The ability of a surgeon to receive dynamic intraoperative magnetic resonance imaging, guiding the surgery, avoiding trauma, and most efficiently treating the diseased tissue is realized using the methodology and system of the present invention.

The ability of a health professional or technician to treat a particular tissue of interest, e.g., using a catheter to insert chemotherapeutic compositions or other treatments, targeting that tissue of interest only, without resort to systemic treatment of the entire organism with attendant toxicity concerns, is better realized using the methodology and system of the present invention.

The ability of a health professional or technician to dynamically monitor the efficacy of a treatment on a tissue of interest by insertion of a magnetic tag or chemical label with the treatment, the characteristics of the magnetic tag and the remaining treatment being visible using MRI, is realized using the methodology and system of the present invention. Likewise, the techniques of the present invention are employed to monitor the extent to which the treatment on said tissue is maintained throughout the course of therapy on the tissue of interest.

BRIEF DESCRIPTION OF THE DRAWINGS

The features, aspects, and advantages of the present invention will become better understood with regard to the following description, appended claims, and accompanying drawings where:

DETAILED DESCRIPTION OF THE INVENTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The present invention is directed to systems and methodologies that use magnetic resonance imaging in treatment. Previous MRI systems, as described above and shown in exemplary FIGS. 1A and 1B, 2A and 2B, although representative of great advancements in the art, also have various disadvantages, focused on access to the patient. In closed MRI systems and prior open MRI systems, images may be taken both before and after surgery, but because of the size of the MRI apparatus and the location of the patient within the MRI apparatus, images may not be taken during surgery and surgeons cannot readily access the patient during imaging, as is necessary during surgery. Thus, MRI has remained a diagnostic tool rather than an essential element of treatment.

The present invention addresses this and other drawbacks. Through advances in design and physics, the present invention describes a system and method for using a room-sized MRI apparatus, allowing surgeons, radiologists, and others complete 360° physical access to a patient for performing MRI-guided surgical and other procedures. By creating a dedicated MRI room, rather than an MRI tube or an open MRI apparatus that allows only minimal access to the patient, the room MRI can be used as an operating or treatment room in order to perform surgical techniques using dynamic and real-time MR imaging, as well as more conventional imaging of patients for diagnostic purposes.

Figure 1A:
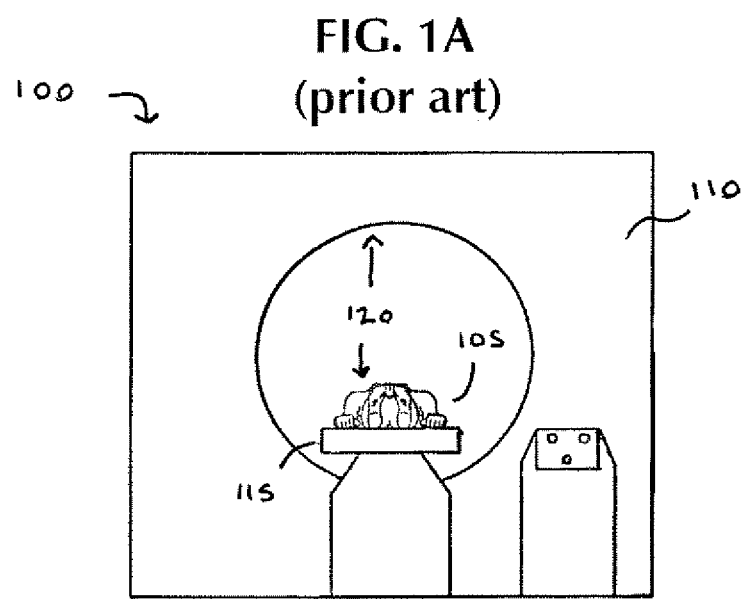
FIGS. 1A and 1B generally illustrate a first generation MRI apparatus.
Figure 1B:
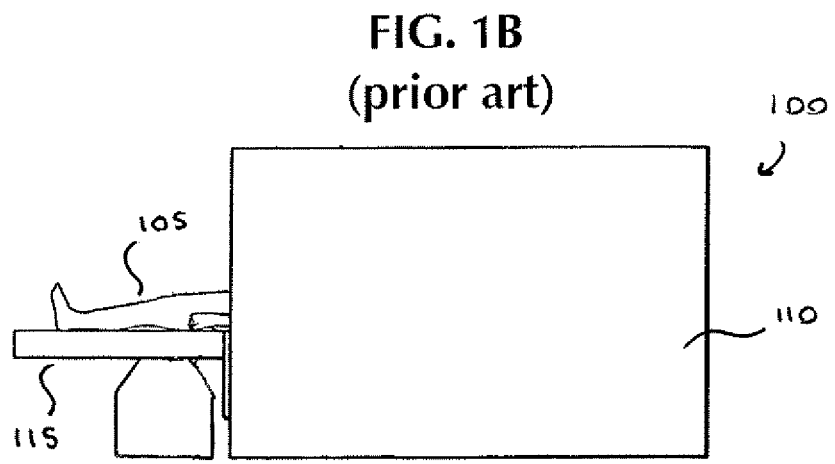
Figure 2A:
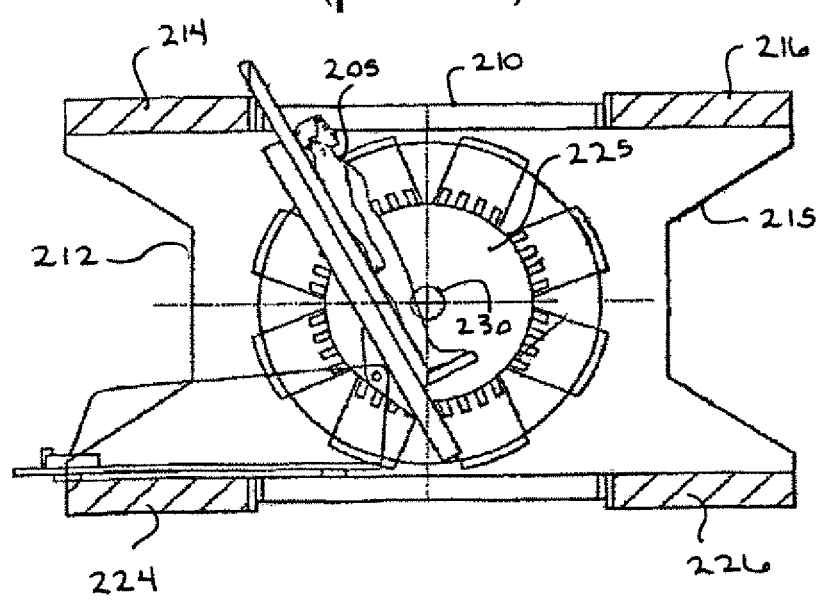
FIGS. 2A and 2B generally illustrate a second generation MRI apparatus.
Figure 2B:
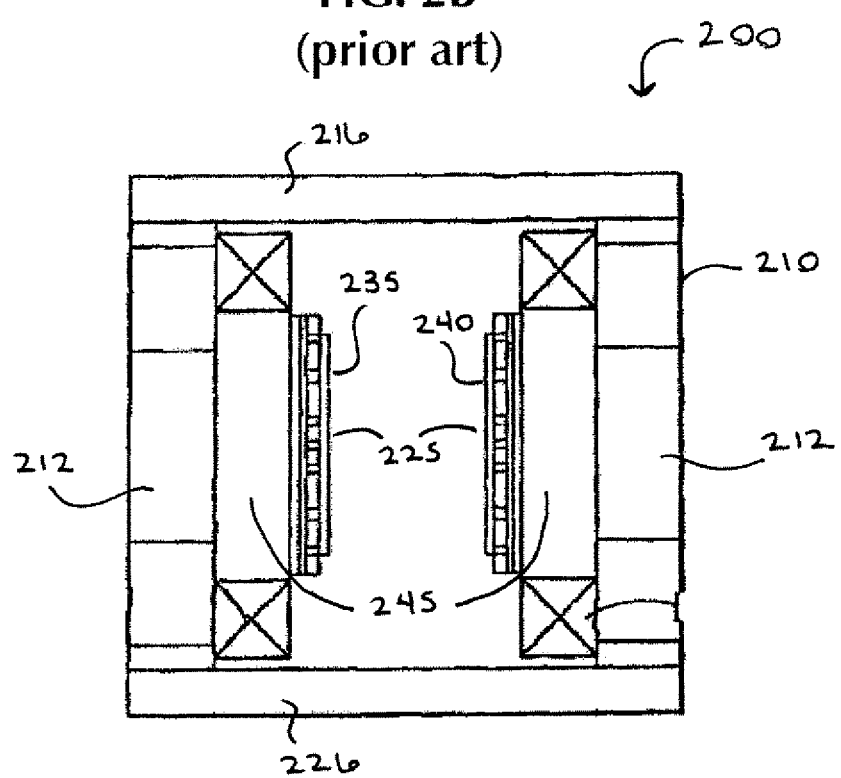
Figure 3:
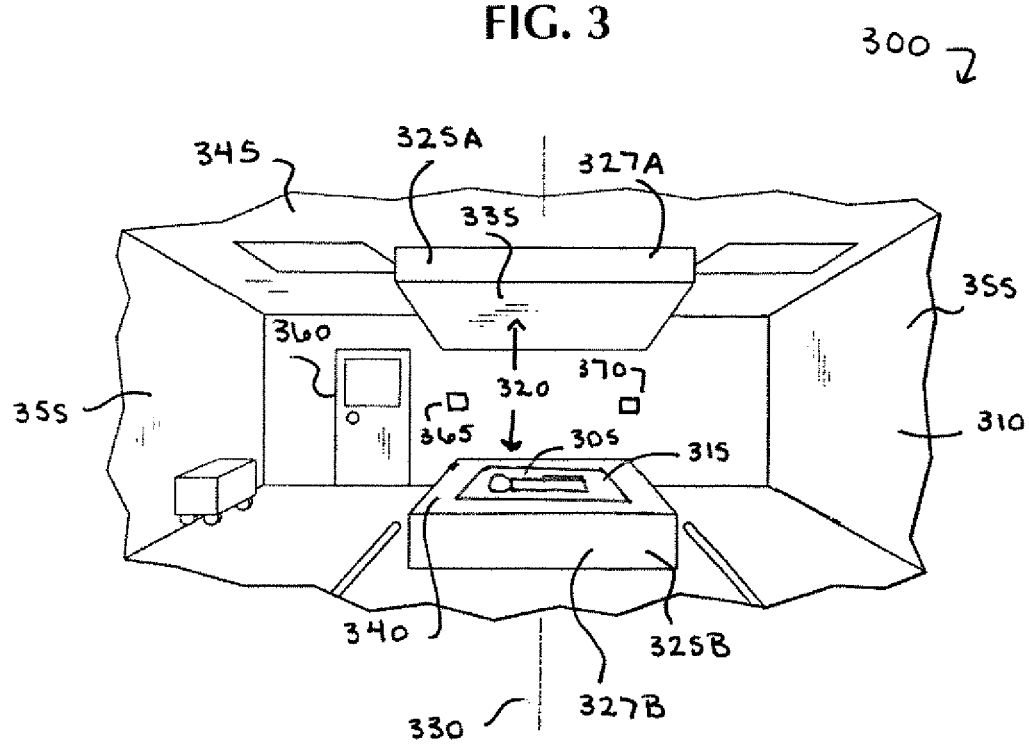
FIG. 3 generally illustrates an open MRI apparatus pursuant to the teachings of the present invention.

With reference now to FIG. 3 of the Drawings, there is illustrated a system, designated generally by the reference numeral 300, in accordance with the present invention. As shown in FIG. 3, a patient, designated generally by the reference numeral 305, is within an MRI treatment room 310. The patient 305 may be a human undergoing a surgical technique or a diagnostic MRI scan. The patient 305 can be diseased, disfigured or ailing in some way, or can be a healthy human. Alternatively, the area of interest for imaging may be only a portion of the patient 305, such as a limb, the head, or a tissue. As shown in FIG. 3, the patient 305 is positioned on a table 315. It should be understood, however, that the patient 305 can be positioned in a variety of positions and the supine position shown is exemplary only, e.g., the patient 305 could be sitting or standing or at an angle.

More particularly, the patient 305 is placed between magnetic poles 325A and 325B, between which a pair of opposed surfaces 335 and 340, respectively, define a gap 320 therebetween, the structure of which is set forth in more detail hereinbelow. The table 315 is a typical operating table constructed of MR-safe materials, or may be any other MR-safe operating apparatus. As stated above, the patient 305 may be placed in any desired position on the table 315 for ease and efficiency during the surgical operation, which is described in more detail hereinbelow and in Applicant's U.S. Pat. No. 6,201,394, which is incorporated by reference herein.

The treatment room 310, likewise, is designed to function as a typical OR room, utilizing MR-safe operating and surgical equipment to conduct minimally-invasive surgical techniques or more serious surgeries using intraoperative dynamically available MRI data. The dimensions of the room are of a typical operating room, configurable with various operating equipment therein, as required. As shown in FIG. 3, the patient 305 is located generally in a central portion of the treatment room 310, generally defining a treatment portion within room 310, with unrestricted access to the patient 305 from all sides around the patient 305 or table 315. It should, of course, be understood that the only fixed portion of the room 310 is the location of the gap 320 between surfaces 335 and 340, allowing ease of access by surgeons and equipment to the patient 305, including the table 315, from an operative space surrounding the treatment portion. More particularly, the configuration and methodology of the present invention provide 360 degrees of access to the patient 305, i.e., totally unrestricted by the physics of the device. With the patient 305 either face up, face down, or on their side, sitting or standing, an MRI image at virtually every angle at any position is possible.

With further reference to FIG. 3, the gap 320 between the pair of opposed surfaces 335 and 340 is at least of sufficient size to accommodate the patient 305 therein and allow total access thereto by others within MRI room 310, e.g., a surgeon or other treatment provider. In one embodiment, the gap 320 is a space of at least 35 cm (14 inches) vertical dimension, preferably at least 48 cm (19 inches) or more vertically (where the poles 325A and 325B are so oriented). It should be understood that the size of the gap 320 is dependent upon a variety of factors, e.g., energy to drive the magnets, patient and staff safety in view of exposure to large field strengths, and other factors. In any event, the patient 305 positioned within the gap 320 within the room 310 can be imaged dynamically or in real-time using magnetic resonance imaging, as described hereinabove. Unlike prior systems, however, the structures of the magnet are configured herein to not constrict the space around the patient 305, i.e., the operative space is substantial and the gap 320 is open for easy access all around the patient 305, i.e., 360 degree access.

As is understood in the art, the surfaces 335 and 340 are the magnetic north and south poles between which the magnetic flux flows. In particular, the surfaces 335 and 340 are part of magnets formed by electromagnetic coil assemblies. The surfaces 335 and 340 are preferably formed by identical electromagnetic coil assemblies and pole caps, and are preferably made of ferromagnetic material designed to suppress eddy currents and to maximize field uniformity, as is known in the art. Some suitable pole designs are described in commonly-assigned U.S. Pat. Nos. 5,061,897, 5,124,651, and 5,592,089, the disclosures of which are incorporated by reference herein.

In the present invention, the surfaces 335 and 340 have a field strength between 0.1 Tesla and 3 Tesla, preferably between 0.5 Tesla and 1.5 Tesla. Generally, magnets with a higher field strength provide a more useful image, but also require larger magnets and surrounding apparatus. An example of such a magnet is described in more detail hereinbelow in connection with FIGS. 9, 10 and 11. It should, therefore, be understood that in the present invention, the magnets used are not limited to small magnets with low fields, but may include mid- and high-field magnets, subject to safety concerns.

As shown in FIG. 3, the surfaces 335 and 340 are illustrated as generally square. The magnet poles 325A and 325B may also be round and cylindrical. The magnet poles 325A and 325B may be covered in shrouds 327A and 327B, respectively, which substantially conforms to the geometrical structure of the outer facings of poles 325A and 325B, thereby forming the aforementioned surfaces 335 and 340 and having an aesthetically pleasing appearance. The patient 305 positioned within the gap 320 between surfaces 335 and 340 within the room 310 can be imaged using magnetic resonance imaging, as described hereinabove. Unlike prior systems, however, the structures of the magnetic poles 325A and 325B and the surfaces 335 and 340 are configured to not constrict the space around the patient 305, i.e., the gap 320 is open for easy access over 360 degrees across the room 310, enabling enhanced therapeutic and clinical treatment possibilities.

In another preferred embodiment, other types of magnets having horizontally-elongated imaging volumes can be employed, forming elliptically-shaped surfaces 335 and 340. In this embodiment, the coils are elliptical rather than square or circular and are elongated in the horizontal direction (following the length of the patient's body) so as to provide a similar horizontally-elongated imaging region. Although in a preferred embodiment the magnetic field volume is elliptical in shape, it should be understood that the present invention is not limited to elliptically-shaped elements poles 325A and 325B.

Alternatively, the surfaces 335 and 340 may also be smaller, with smaller scanning areas for smaller areas of interest, such as the brain or another tissue or organ. Thus, while the MRI room 310 is configured in a similar manner, with a substantial free operative space around the entire MRI imaging area, the imaging area is smaller and focused on a small portion of the patient 305, rather than upon the entire body of the patient 305. It should be understood that with smaller volumes for imaging, substantially and actual real time imaging can take place with particular waveforms and other parameters.

As shown in FIG. 3, the opposing surfaces 335 and 340 are preferably aligned about a polar axis 340. The surfaces 335 and 340 are disposed at or near the ceiling and floor portions, respectively, designated generally by the numerals 345 and 350, of the room 310, respectively, thereby best conforming to the shape.

It should, of course, be understood that the surface 335 may extend from the ceiling 345, and the surface 340 may extend from the floor 350. In a preferred embodiment, at least the surface 340 is flush with the floor 350, thereby permitting ease of movement along the plane of the floor whether within the gap 320 or thereabout. In another preferred embodiment, the surfaces 335 and 340 are flush with the ceiling 345 and floor portions 350, respectively, allowing fully unrestricted and 360 degree access to the patient 305. In another preferred embodiment, the surface 340 is raised from the floor 350, thereby substantially or actually acting as the table or bed 315, for positioning the patient 305 thereon. In a presently preferred embodiment, surfaces 335 and 340 both extend from the ceiling 345 and floor 350, respectively, thereby minimizing the gap 320 and field strengths necessary to image the patient 305, while simultaneously providing full and unrestricted 360 degrees access to the patient 305.

The ceiling 345, floor 350, and the side walls, generally designated by the reference numeral 355, are preferably formed from non-magnetic materials such as polymeric materials, wood fibers, paper and cement materials such as concrete, plaster, plasterboard, etc., as is understood in the art. The exposed ceiling 345, floor 350, and walls 355, thus, have the appearance of a standard room, from an architectural perspective, and may be of any size. Pursuant to the teachings of the present invention, the size of the room is sufficient to enable normal operational and other treatments on patients situated therein, i.e., the operating space (room space surrounding the treatment portion, which is the patient 305 or table 315).

Magnetic shielding, active or passive, is used to limit the magnetic flux, and is located in the walls 355 or outside the room 310, as well as in the ceiling 345 and floor 350 to protect both horizontally- and vertically-adjacent rooms. Generally, the shielding restricts the magnetic flux from traveling beyond the MRI room 310, as well as protecting the room 310 from stray RF signals, as is known in the art. The shielding is preferably in the form of a ferromagnetic structure surrounding the room 310, e.g., built into the wall structures. The ferromagnetic structure guides the magnetic flux from the magnets and prevents the flux from traveling away from the MRI operating room 310 and possibly interfering with or damaging devices outside of the MRI operating room.

Additionally, the room 310 is preferably surrounded with a continuous or substantially continuous electrically conductive shield, known as a Faraday shield, which shields the operating room 310 and the MRI from RF interference, as is known in the art. The ceiling 345, floor 350, and walls 355 of the room 310 are preferably provided with conductive elements, such as conductive mesh, connected to the frame of the magnet assembly. Any gaps in the walls 355 of the room 310, such as a door or window 360, are preferably also provided with a conductive covering, such as a conductive mesh or film.

In installations where vibrations are of concern, the entire room 310 may be vibrationally isolated, such as by structures flexibly supporting the room 310, as is known in the art.

Further elements of the MRI, including the gradient coils may be conventionally located in proximity to the poles. With further reference to FIG. 3, there is illustrated a gradient coil 365 adjacent said gap 320 for applying magnetic field gradients therethrough.

The RF transceiver and antennas may be conventionally located on the patient support 315, or otherwise near the patient 305. As shown in FIG. 3, one or more transmitters and receiving antennae 370 are also provided adjacent said gap 320 for transceiving MRI data.

An exemplary MRI room 310 of the present invention, recently tested and built in Oxford, England, has the room dimensions of: a ceiling height of 8 feet, a width of 14 feet, and a length of any desired dimension. For example, with reference to FIG. 3, the floor 350 to ceiling 345 height is eight feet and the width (perspective perpendicular to the FIGURE) is fourteen feet. The remaining dimension (perspective horizontal in the FIGURE) is variable, e.g., twenty feet or more. The gap 320 is 19 inches and the surfaces 335 and 340 extend from both the ceiling 345 and floor 350, as illustrated in FIG. 3 and described in more detail hereinbelow. In this illustration of usage of the present invention, the MRI room 310 operates at 0.6 Tesla and 25.5 MHz. As is apparent to one skilled in the art, these measurements are exemplary and may be varied according to desired operating parameters. As indicated, the exemplary room has full 360° unrestricted access to the patient.

Figure 4:
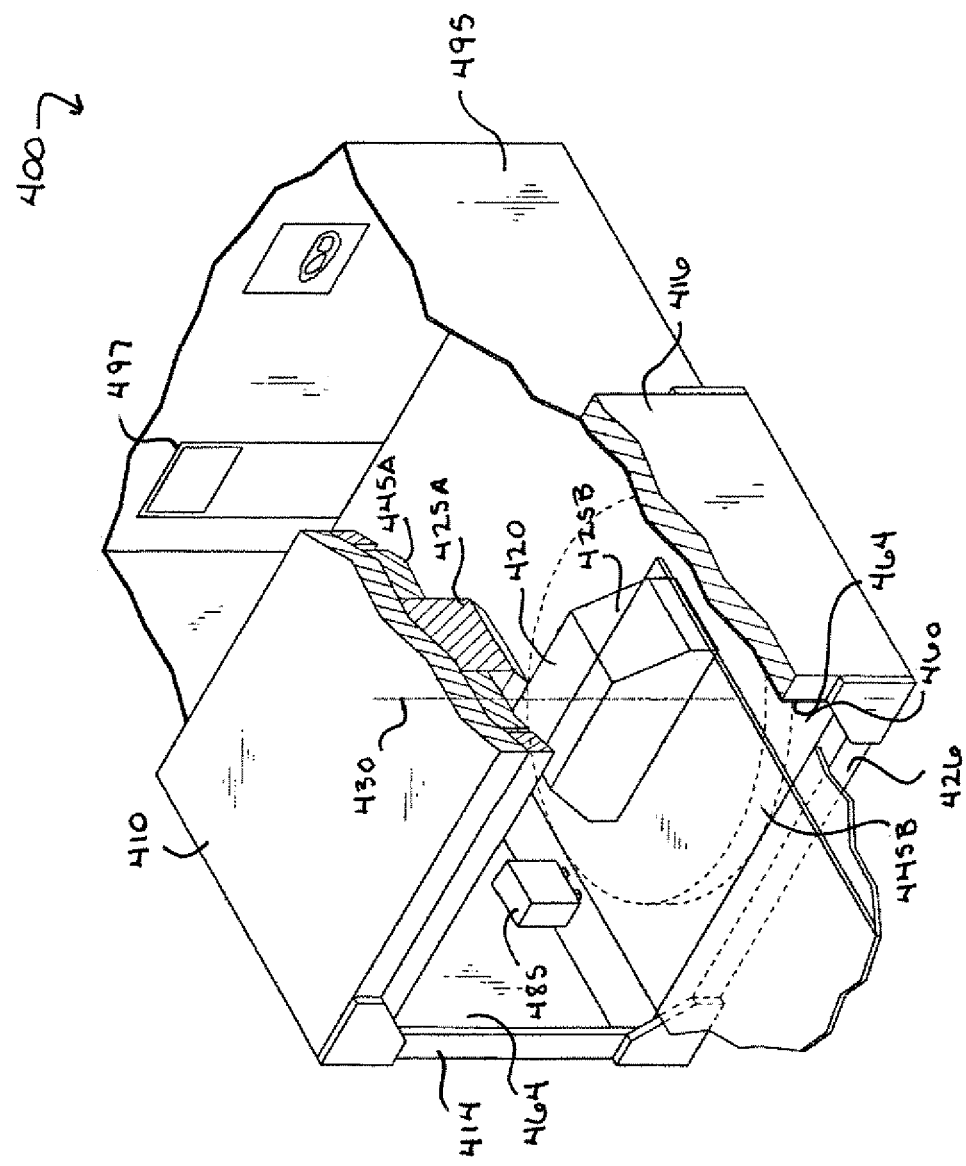
FIG. 4 shows an exemplary embodiment of the MRI apparatus of the present invention.
Figure 5:
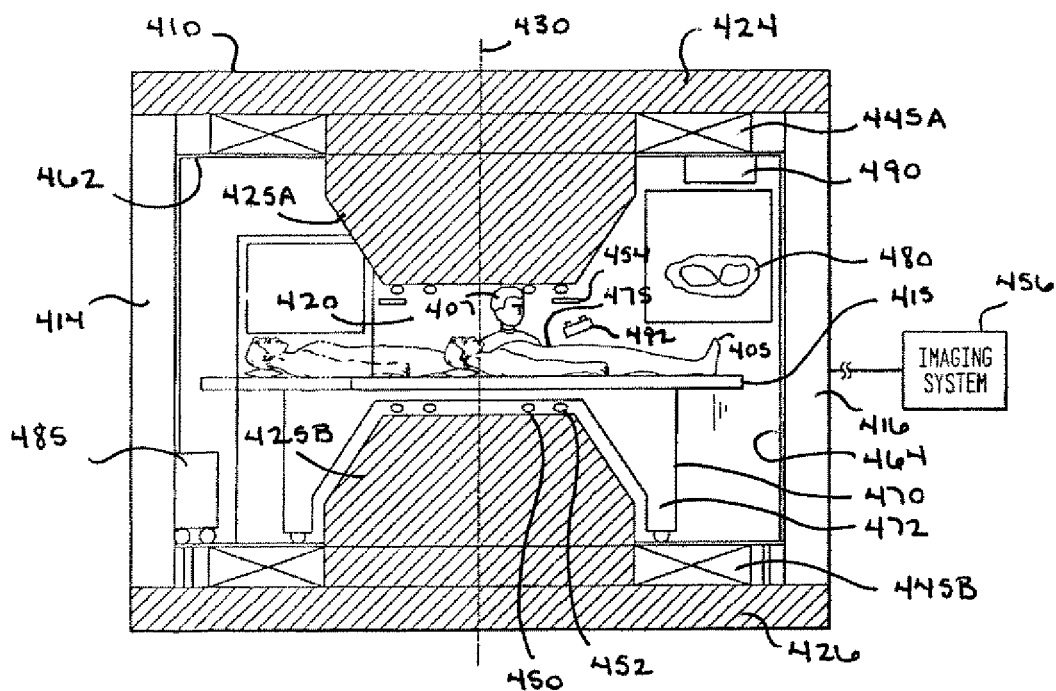
FIG. 5 shows a side view of the exemplary embodiment of FIG. 4.

With reference now to FIGS. 4 and 5, there are illustrated additional embodiments and descriptions of magnets and MRI rooms pursuant to the teachings of the present invention, and in view of the recent advancements in the technology. As shown in FIGS. 4 and 5, the MRI system, generally designated by the reference numeral 400, has an MRI room 410 made of connecting elements 414 and 416 disposed about seven feet from a polar axis 430 centered between the poles 425. Each of the connecting elements 414 and 416 is a steel slab approximately nine feet tall, ten feet wide, and 12 inches thick. Unless otherwise specified, the distance between the polar axis 430 and the connecting elements 414 and 416 specified herein should be understood as referring to the smallest distance from the polar axis 430 to any connecting element in a direction perpendicular to the polar axis 430, measured at the medial plane of the apparatus such as the radial distance shown in FIGS. 4 and 5, i.e., from the polar axis 430 to the nearest side wall. Because the connecting elements 414 and 416 are disposed at substantial distances from the polar axis 430, an adult human patient 405 can be positioned on a support, such as a litter or bed 415 (FIG. 5) in a generally horizontal position with his or her body extending close to the medial plane and generally parallel thereto, and the patient 405 can be disposed in any radial direction with any part of his or her body relative to the polar axis 430. Thus, essentially any part of a normal human patient can be imaged from almost any angle of observation.

In further reference to FIG. 5, the apparatus in accordance with a preferred embodiment of the invention includes an upper pole support 424 and a lower pole support 426. Each of these pole supports 424 and 426 preferably includes a steel slab approximately sixteen feet long, ten feet wide, and about twelve inches thick. The upper pole support 424 is held above the lower pole support 426 by said connecting elements 414 and 416. As indicated, each of the connecting elements 414 and 416 is a steel slab approximately nine feet tall, ten feet wide, and 12 inches thick. Ferromagnetic connecting elements 414 and 416 are disposed between the pole supports 424 and 426 at the ends thereof, so that the upper pole support 424 lies approximately eleven feet above the lower pole support 426 and so that the inwardly-facing surfaces of the connecting elements 414 and 416 are spaced apart from one another by a distance of approximately fourteen feet in this embodiment. As best appreciated with reference to FIG. 4, the pole supports 424 and 426 and the connecting elements 414 and 416 form four sides of a rectangular box, i.e. the MRI room. As is understood in the art, elements 424, 426, 414 and 416, in combination, provide the flux return path. Gusset plates are provided at the corners of the box or MRI room 410 to reinforce it against racking and twisting stresses.

As shown in FIGS. 4 and 5, an upper ferromagnetic pole 425A projects downwardly from upper pole support 424, whereas a lower ferromagnetic pole 425B projects upwardly from the lower pole support 426. Poles 425A and 425B are generally in the form of rectangular solids. As best seen in FIG. 5, the upper ferromagnetic pole 425A tapers as it moves away from the pole support 424. The lower ferromagnetic pole 425B likewise tapers as it moves up from the lower pole support 426. The taper or progressive reduction in the long dimension of the poles minimizes saturation in the pole stem and aids in providing a uniform field even with relatively narrow poles having a small short dimension.

The narrow poles provide better access to the patient for the physician or surgeon. The proximal portion of the lower pole 425B has rounded corners. The proximal portion of the upper pole 425A has similar rounded corners. Both poles 425A and 425B are aligned with one another and define said polar axis 430 extending vertically, transverse to pole supports 424 and 426, through the centers of the poles 425A and 425B. The long dimensions of the poles 425A and 425B are aligned with one another so as to provide an elongated patient receiving gap 420 between the poles 425A and 425B. The pole tips desirably have a ratio of long dimension to short dimension of about 4:3 or more, and more preferably about 1.5:1. For example, the pole tips may have dimensions of about 48 inches (1.22 m) by about 72 inches, whereas the pole bases may also be generally rectangular and may have dimensions of about 48 inches (1.22 m) by about 86 inches (2.18 m). The distance between the pole tips and hence the dimension of gap 420 in the axial direction along polar axis 430 desirably is at least about 17.5 inches and more desirably about 36 inches. The ratio between the shortest dimensions of the pole tips and the dimension of the gap 420 in the axial direction is most preferably about 1.3:1. This ratio desirably is about 1:1 and about 2:1 or less.

A resistive electromagnet coil 445A encircles the stem of upper pole 425A at its juncture with the upper pole support 424. A corresponding lower resistive electromagnetic coil 445B encircles the stem of the lower pole at its juncture with lower pole support 426. The electromagnetic coils 445A and 445B are also generally rectangular in shape. In this example, each one of the coils may have a width of about 33 inches and a thickness of about 12 inches. This large area keeps resistive power losses low. For superconducting coils, this area will be greatly reduced.

The apparatus also includes the other components conventionally utilized in MRI apparatus. For example, in FIG. 5, gradient coils 450 are disposed adjacent gap 420 for applying magnetic field gradients. Shimming coils 452 are disposed adjacent gap 420 for providing an additional magnetic field which enhances the uniformity of the magnetic field in the gap. One or more RF transmitting and receiving antennas 454 is also provided adjacent gap 420. The components described above are linked to a conventional MRI imaging system 456 including elements such as a DC power supply for energizing coils 445A and 445B and shimming coils 452; RF transmitters and receivers linked to antennas 454; and gradient coil power devices linked to gradient coils 450. The apparatus 410 also is provided with a conventional control computer and conventional components for transforming the received magnetic resonance signals into the desired images. Such elements are well-known in the MRI art and need not be described further herein.

The apparatus further includes a raised floor 460 supported above the lower pole support 426. Floor 460 extends over the top of the lower coil 445B. A ceiling 462 is suspended beneath upper pole support 424. Wall coverings 464 may be provided on the inwardly facing surfaces of connecting elements or walls 414 and 416. Floor 460, ceiling 464 and wall coverings 464 preferably are formed from non-magnetic materials such as polymeric materials, wood fibers, paper and cementitious materials such as concrete, plaster, plasterboard and the like. The exposed, inwardly-facing surfaces of the floor 460, walls and ceiling 462 desirably are formed from standard architectural materials and have the appearance of ordinary room walls. Ceiling 462, wall covering 464 and floor 460 may have standard architectural features such as built-in lamps.

With reference now to FIG. 4, floor 460 may be continuous with the floor of a building in which the apparatus is located. Wall covering 464 may be continuous with the walls of the building. Likewise, ceiling 462 may be continuous with a ceiling which is part of the building. Thus, the space within the magnet enclosed by floor 460, ceiling 462 and wall covering 464 constitutes part of an ordinary room. The magnet frame, including the pole supports 424 and 426 and the connecting elements 414 and 416 are disposed outside of the room. Also, the coils 445A and 445B are disposed outside of the room. In variants where the interior wall coverings 464, ceiling 462 and floor 460 are not provided, elements of the ferromagnetic frame themselves may define the interior wall surfaces of the room. For example, where wall covering 464 is omitted, the inwardly-facing surfaces of connecting elements 414 and 416 define the interior wall surfaces of the room. In this case as well, the remainder of the connecting element lies outside of the room.

As is understood in the art, the pole supports 424 and 426, connecting elements 414 and 416, and poles 425A and 425B are arranged to provide a path with low magnetic reluctance for the flux generated by coils 445A and 445B. The flux is relatively concentrated in the poles 425A and 425B and in regions of the upper and lower pole supports 424 and 426 adjacent the polar axis 430. Thus, the magnetic field achievable with the magnet may be limited by magnetic saturation of the ferromagnetic material in these regions. Magnets according to the present invention typically provide fields of at least about 0.5 kilogauss, preferably at least about 1 kilogauss, more preferably at least about 3 kilogauss and desirably at least about 6 kilogauss in gap 420, but may include magnets operating at considerably higher field strengths. For example, to provide a field of about 6 kilogauss, each of coils 445A and 445B may include about 220 turns, and may be energized at a current of about 1,000 amperes to provide about 220,000 ampere-turns each. Ferromagnetic material of relatively high permeability, preferably equal to or greater than the permeability of grade 1006 steel is used in the central regions of the pole supports 424 and 426 and in the poles 425A and 425B. Preferably, the high permeability magnetic material has a permeability of at least about 50 at a field strength of 20 kilogauss or higher within the ferromagnetic material. Very high permeability materials, such as grade 1001 steel, having a permeability in excess of 50, at a field of 22 kilogauss is even more preferred.

In the regions of the pole supports 424 and 426 remote from the polar axis 430 and in the connecting elements 414 and 416, the magnetic flux spreads out over the entire width and thickness of the ferromagnetic material. Therefore, the magnetic flux is substantially less concentrated in these regions and magnetic material of lower permeability can be used if desired. Moreover, because the pole supports 424 and 426 and connecting elements 414 and 416 are disposed outside of the space occupied by the patient 405 and the attendant 407, the size of these elements is essentially unlimited. Adding more material does not impede access to the patient. Thus, essentially any ferromagnetic material of modest magnetic conductivity can be provided in these elements without impairing access to the patient, simply by providing more ferromagnetic material. Accordingly, in these regions of the frame, the choice between using a relatively thin element at high permeability material and a thick element of lower permeability material is controlled by considerations such as economics and the weight of the resulting structure.

Coils 445A and 445B may be replaced by superconducting coils. Superconducting coils typically are enclosed in vessels referred to as cryostats filled with a coolant, such as liquid helium for conventional low temperature superconductors such as NbTi or $Nb_3Sn$ or, preferably, liquid nitrogen for high temperature superconductors. The coolant maintains coils at temperatures low enough to provide superconductivity. The required temperature of course depends upon the composition of the superconducting material. Preferred promising superconducting materials such as BSCCO and YBCO provide superconductivity at temperatures of about 77° K, the boiling point of liquid nitrogen, or at even higher temperatures (see for example Superconductive Components, Columbus, Ohio, Eurus Technologies, Inc., Tallahassee, Fla.). This minimizes the amount of energy which must be expended to cool the coils and also greatly simplifies the design of the cryostats and associated components. The superconducting coils in their cryostats include the poles 425A and 425B in the same positions as conductive coils 445A and 445B, for example, located above the ceiling 462 and below the floor 460. Thus, the operative space desirably extends above one cryostat and below the opposite cryostat. However, for very high current densities, small cross-section coils may alternatively be located surrounding the poles 425A and 425B in place of the blocking magnets discussed below with reference to FIG. 8. As described, for example, in U.S. Pat. No. 4,766,378, use of a ferromagnetic frame with projecting ferromagnetic poles in conjunction with superconductive coils is particularly advantageous. The ferromagnetic frame tends to stabilize the superconducting coil and reduce field non-uniformities caused by coil movement. The present invention thus affords a way to attain the benefits disclosed in the '378 patent while also providing essentially unlimited access to the patient. Superconducting coils can be used for low fields but are particularly useful where a very high magnetic field, above about 6 kilogauss is desired within the gap.

With reference again to FIG. 5, a patient positioning device 470 may be utilized with the magnetic resonance imaging system and magnet 400 to position the patient 405 relative to the poles 425A and 425B and magnet gap 420. Device 470 desirably is formed from non-magnetic materials such as polymers. The positioning device 470 includes a chassis 472 mounted on wheels. As best seen in FIG. 5, chassis 472 includes a pair of vertically-extensive end portions which lie on opposite sides of the lower pole 425B when the chassis 472 is aligned with the polar axis 430 of the magnet. A bridge position of the chassis 472 extends between the end portions, and overlies pole 425B when the chassis 472 is aligned with the polar axis 420. Brakes on wheels or other devices for holding chassis 472 in position may be provided. In addition, the adjacent portions of the floor 460 may be provided with graduations, and chassis 472 may be provided with a point or other index mark so that the chassis 472 can be brought to a pre-selected disposition in the first movement or Z direction. Other positioning devices, such as a screw jack, fixed or adjustable stop or optical positioning system may be employed to locate and index the position of the chassis relative to the floor and the magnet frame. A specialized patient positioning device, such as that found in U.S. Pat. No. 6,944,492 may also be used.

Figure 6:
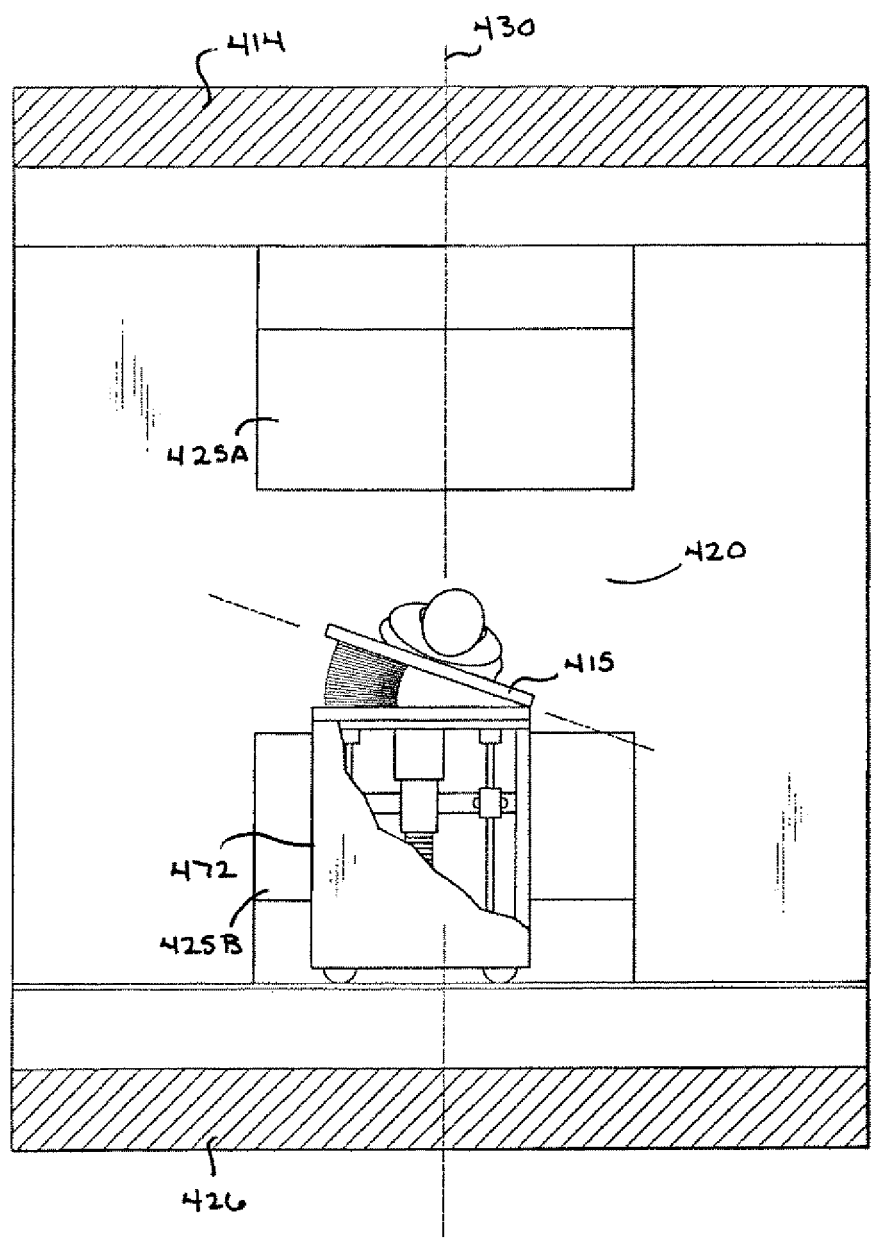
FIG. 6 shows an alternate side view of the exemplary embodiment of FIG. 4.

The ability to position the patient in essentially any arbitrary location and position relative to the magnet, and relative to the vertical is extremely desirable both in imaging and in image-guided surgery. Certain surgical procedures are best performed in certain orientations of the patient. As shown in FIG. 6, a patient may be treated at an angle. Also, the best images of the patient are acquired in the region immediately adjacent the polar axis. Therefore, the region of interest of the patient may be positioned at the polar axis to assure optimum imaging of the region of interest.

Figure 7A:
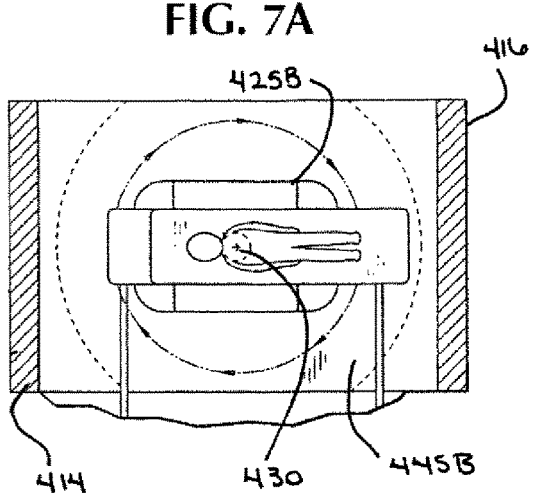
FIGS. 7A-7D show top views of the exemplary embodiment of FIG. 4.
Figure 7B:
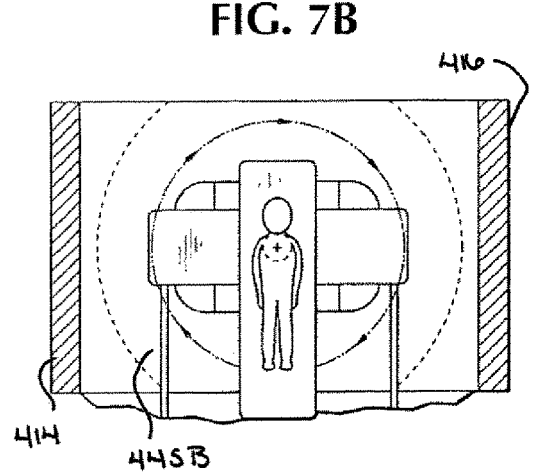
Figure 7C:
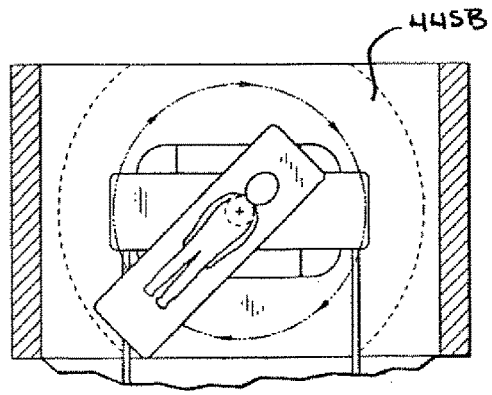
Figure 7D:
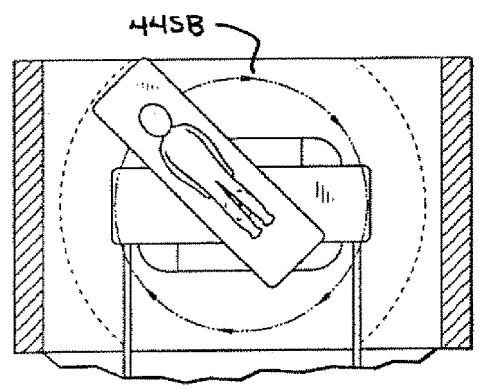

An upper member 608 is mounted on chassis 472. As shown in FIG. 6, screw jack 610 or other mechanical positioning system such as a hydraulic or pneumatic cylinder, lever system or the like is also provided for moving upper member 608 vertically, in the axial or Y direction, parallel to the polar axis 430 of the magnet. Positioning device 610 may be arranged to displace upper member 608 relative to the remainder of the chassis 472. Alternatively, upper member 608 may be fixed to the remainder of the chassis and positioning device 610 may be adapted to move the chassis 472 relative to wheels. An elongated, movable support 612 is mounted for pivoting movement relative to the chassis 472 and upper member 608 around a pivot 614, as shown in FIG. 7A. Pivot 614 is close to the center of the chassis 472. Thus, when the chassis 472 is positioned in the Z direction so that the center of the chassis 472 is coincident with the polar axis 430, the pivot 614 is also close to the polar axis 430. Movable support 612 is also mounted for sliding motion relative to upper member 608 and chassis 472 in a longitudinal direction X, parallel to the long direction of the support itself. Thus, as seen in FIGS. 7A through 7D, the movable support 612 can swing in pivoting motion around pivot 614 so as to orient the longitudinal direction X at any desired angle to the first movement direction Z. Thus, the longitudinal direction X of the movable support can be oriented in any direction relative to the long axis of the rectangular poles 425A and 425B. By moving the movable support relative to the chassis 472 in its longitudinal direction, various locations along the length of the movable support 612 can be aligned with the polar axis 430 of the magnet.

Additionally, the litter or actual patient-carrying device 415 is mounted to the movable support 612 for pivoting movement around a tilt axis 616 parallel to the longitudinal or X direction of the movable support. Thus, as seen in FIG. 6, the tilt axis 616 extends into and out of the plane of the drawing. A tilt actuation device 618, such as a pneumatic bladder or pneumatic cylinder, screw jack, or wedge jack, is provided for tilting the litter through a range of tilt angles. The patient support is also pivotable relative to the movable support about an inclination axis 617 transverse to the lengthwise direction of the support and transverse to the tilt axis. An inclination actuator (not shown) similar to the tilt actuator is provided for pivoting the support about the inclination axis. This allows positioning of the patient in a Trendlenburg or counter-Trendlenburg position. Thus, the patient positioner 470 provides litter or support 415 with movement in six degrees of freedom: translation in a first lateral direction Z transverse to the polar axis 430; translation in the X or longitudinal direction of the movable support 612, also transverse to polar axis 430 and at an arbitrary angle to the first or Z direction; rotation in a horizontal plane transverse to the polar axis 430 so as to orient the longitudinal direction X at any angle B relative to the long axes of the poles 425A and 425B; elevation or axial movement Y parallel to the polar axis 430, illustrated in FIG. 6; tilt to any desired angle to the horizontal plane; and inclination so as to raise either end of the support. This provides extraordinary versatility in positioning of the patient relative to the magnet. For example, as seen in solid lines in FIG. 5, the head and neck of the patient 405 is substantially aligned with the polar axis 430. Translation in the longitudinal direction allows positioning of the feet adjacent the polar axis 430, as seen in broken lines in FIG. 5. Other, arbitrary positions of the patient relative to the polar axis 430 and relative to the remainder of the magnet are also shown in FIGS. 7A through 7D. Of course, the large clearance within the magnet provided by the ferromagnetic frame discussed above also contributes to the positioning versatility. Because the connecting elements 414 and 416 are spaced at a radial distance from the polar axis 430 of about seven feet or more, longitudinal movement of the patient 405 relative to the frame can be accommodated over a range sufficient to position essentially any part of the patient's body at the polar axis 430.

As illustrated in FIG. 5, the physician 407 is performing an MRI-guided medical procedure on the patient 405. In this instance, the physician 407 is advancing a surgical probe 475 having an MRI-visible tip into the body of the patient 405. The imaging system and MRI magnet are operating so as to continually prepare new images of the patient 405. These images include an image 480 of the surgical probe 475, also showing the patient's internal structures. Thus, as the probe 475 and the internal structures of the patient 405 move, the displayed image 480 including the representation of the probe 475 continues to portray the correct relative positions of the probe 475 and internal structures intraoperatively. The physician 407 therefore can use this image 480 for guidance as he or she moves the probe 475 and conducts the procedure. Of course, as MRI can also show different tissues within the body in contrast, the physician 407 can use the image 480 of the body structures for guidance in performing the treatment. For example, where a surgical operation is performed to treat a tumor, the MRI system can be operated to acquire an image which shows the tumor in contrast to surrounding normal tissue. The image contrast can be used to monitor the success of the therapy. These capabilities are particularly valuable in performing minimally-invasive procedures, i.e., procedures which only a relatively small probe, such as an endoscope or catheter is advanced into the body, percutaneously or through a small surgical opening or a natural body orifice. Examples of such probes 475 are set forth in more detail hereinbelow. Of course, other medical and surgical procedures can be performed while the patient 405 is disposed in the magnetic gap 420 and while MRI imaging is conducted.

The environment within the magnet frame constitutes an operating or treatment room, and desirably includes the features normally found in operating and treatment rooms as, for example, proper lighting sanitation features, life support systems and other surgical apparatus. The essentially unimpeded access to the patient 405, and freedom of patient positioning provided by the magnet and patient positioning system 470 greatly facilitate performance of these and other medical procedures while the patient is continually imaged by the MRI system. Of course, because MRI does not use ionizing radiation, such as X-rays, properly conducted MRI procedures pose little or no appreciable health risk to the patient 405 or to the physician 407. The magnetic fields impinging on the physician 407 standing in the work space are minimal. The projecting ferromagnetic poles 425A and 425B concentrate the flux flowing from pole to pole in gap 420, substantially between the poles 425A and 425B. The ferromagnetic flux return path, including the pole supports 424 and 426, and the connecting elements 414 and 416, carries the vast majority of the returning flux. Moreover, the substantial space between the poles 425A and 425B and the connecting elements 414 and 416 tends to minimize flux leakage from the poles 425A and 425B to the connecting elements 414 and 416. Therefore, where the physician 407 is located, the field is minimized. To the extent that any risk is associated with exposure to such magnetic fields, the risk is, therefore, diminished. Moreover, because only a very small portion of the magnetic flux passes outside of gap 420 between the poles 425A and 425B, movement of non-ferromagnetic metallic objects outside of the gap 420 will not induce substantial eddy currents in such equipment. There is minimal magnetic interference with medical equipment disposed in the operative space.

The space around poles 425A and 425B provides an unobstructed operative space sufficient to accommodate a physician 407 or other adult human 405. This space is unobstructed by any portion of the magnet frame and extends entirely around the poles 425A and 425B and polar axis 430. Thus, apart from any obstructions which may be created by the patient support 415 or the patient 405 himself, the attendants 407 can have access to the patient 405 from all locations. This operative space extends to the region of the magnet between coils 445A and 445B. Thus, a portion of the operative space is disposed above the lower coil 445B and below the upper coil 445A. The degree of access afforded by the apparatus is essentially the same as the degree of access provided in an ordinary operating room, with only a slight obstruction caused by poles 425A and 425B themselves. That obstruction is minimized by the relatively small diameter of the poles 425A and 425B and the relatively large space between the poles 425A and 425B.

Equipment for performing medical procedures on a patient, such as an anesthesia ventilator 485 illustrated in FIG. 5, or any other type of conventional medical equipment may be situated inside the room, within the interior of the magnet frame. Further, a display device, such as a projection unit 490 as shown in FIG. 5, is connected to the computer associated with the MRI system and is desirably mounted to display an image 480 inside the room, so that a physician 407 or other persons performing medical procedures on a patient 405 within the apparatus can observe the MRI image in real time, while performing such procedures. The projection unit 490 is a particularly desirable display because it provides a large image which can be seen by all members of the medical team in the room. One or more conventional CRT monitors and/or video goggles, as discussed below, can also be utilized. Control apparatus 492 such as a keyboard, joystick, mouse, or touch-sensitive elements on a monitor may also be provided inside the room 410, so that the attendant 407 can control the MRI imaging process from within the room 410.

Preferably, the operative space and gap 420 are shielded from radio frequency interference, to prevent interference with MRI imaging procedures. Thus, the room preferably is surrounded with a continuous or substantially continuous electrically conducted shield, i.e., a Faraday shield, as discussed in more detail hereinabove. Because the pole supports 424 and 426 and connecting elements 414 and 416 of the magnet frame are electrically conductive, these elements may serve as a portion of the Faraday shield. In addition, the floor 460 and walls of the building, as well as the ceiling 462 of the room 410 may be provided with conductive elements, such as a conductive mesh 495 illustrated in FIG. 4. The conductive mesh 495 may be electrically connected to the magnet frame as by a wire or bonding strap connecting the mesh to the frame. Doors 497 and windows penetrating these walls are also provided with conductive coverings, such as mesh 495 in the doors 497 and conductive films on the windows. These conductive coverings desirably are also connected to the remainder of the Faraday shield. The equipment disposed inside of the room 410, and hence inside of the Faraday shield is designed for low RF emission. For example, the video monitor 490 may be provided with an enclosure having a conductive shield which is grounded to the frame. Also, fixtures such as overhead lights may be provided with a similar shielding.

Figure 8:
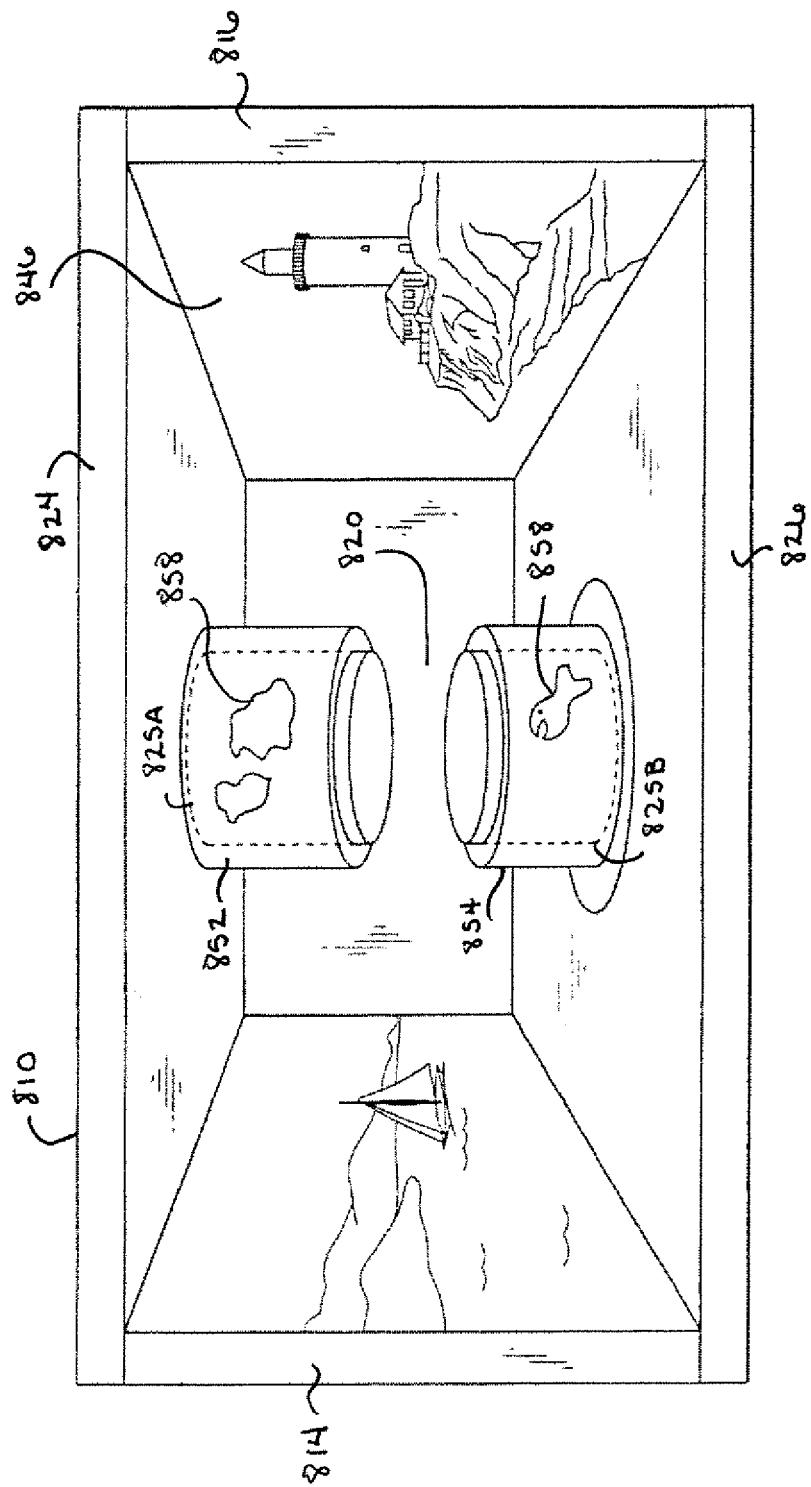
FIG. 8 shows an exemplary embodiment of the MRI apparatus of the present invention.

The magnet depicted in FIG. 8 is generally similar to the magnets discussed above. The magnet of FIG. 8 has a pair of horizontal plate-like pole supports 824 and 826 and a pair of plate-like connecting elements 814 and 816 extending between the pole supports 824 and 826. Here again, the pole supports 824 and 826 and connecting elements 814 and 816 at least partially enclose a room 810. As the interior surfaces of the pole supports 824 and 826 and connecting elements 814 and 816 are the bounding surfaces of the room 810, the connecting elements 814 and 816 and pole supports 824 and 826 themselves are disposed outside of the room 810.

Generally cylindrical poles 825A and 825B project into the room from the floor and ceiling of the room. Here again, the room is large enough to accommodate both the poles and patient-receiving gap 820 together with an operative space sufficient to accommodate one or more physicians. As discussed above, the physicians in the operative space will have essentially unrestricted access to the patient. Moreover, the entire magnet provides a non-claustrophobic experience to the patient.

The magnet of FIG. 8 includes concealment structure in the form of surface ornamentation including pictures 846 on interior surfaces of the room. In this case, the pictures are disposed on the interior surfaces of the connecting elements 814 and 816 defining side walls of the room as well as on a non-ferromagnetic, non-functional rear wall. The magnet structure further includes pole covers 852 and 854 overlying the poles 825A and 825B and associated structures such as coils encircling the poles. The pole covers may also be provided with pictures 858. Desirably the pictures on the interior surfaces of the room and on the pole covers from a unified scene, as for example, the marine scene depicted in FIG. 8 or some other type of outdoor scene. The scene desirably includes a depiction of a sky extending unto the ceiling of the room as, for example, in the inner surface of the upper pole support 824 and may also include a natural-appearing earth tone or water tone on the floor, i.e., on the upper surface of lower pole support 826. In the embodiment of FIG. 8, these concealing pictures are painted directly unto the surfaces of the metallic frame elements. However, the same pictures may be provided on other walls, floors or ceilings defining a room within the frame, as for example, on the wall coverings 464 discussed above with reference to FIG. 4, or on ceiling or floor coverings. In still further embodiments, the pictures may be dynamically provided as, for example, by a still projector, motion picture projector, projection television system, or computer-based projector which displays static or moving pictures on the exposed interior surfaces of the room. The pictures enhance the patient's experience during the procedure.

Figure 9:
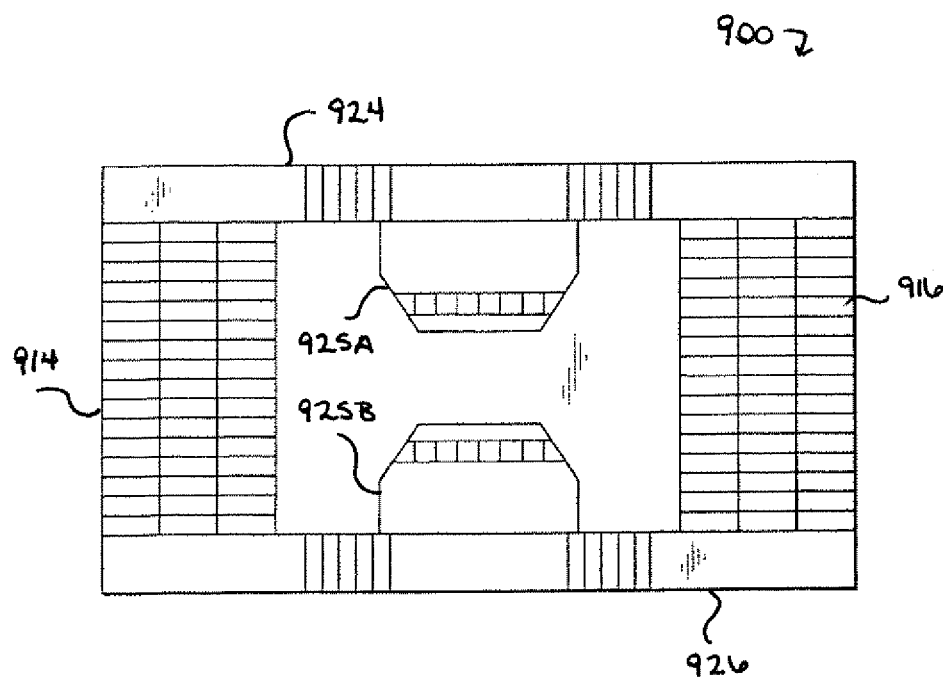
FIG. 9 shows an exemplary embodiment of the MRI apparatus of the present invention.

As shown in FIG. 9, an apparatus according to another preferred embodiment of the invention, utilizes a frame, generally designated by the reference numeral 900 having permanent magnets as the source of magnetic flux. For example, connecting elements 914 and 916 in this embodiment include magnetic blocks formed from a "hard" magnetic material, i.e., a magnetic material having high coercivity, which is resistant to demagnetization. Alternatively or additionally, permanent magnets may be provided in the upper pole support 924, in the lower pole support 926, or in poles 925A and 925B themselves. Here again, because the pole supports 924 and 926 and the connecting elements 914 and 916 are disposed outside of the operative space, and outside of the space occupied by the patient, there is essentially no physical limit on the size of these elements. Therefore, these elements may incorporate essentially any amount of permanent magnet material. This facilitates the use of relatively low-energy magnet materials as an alternative to high energy product materials to provide some or all of the magnetic flux.

Figure 10:
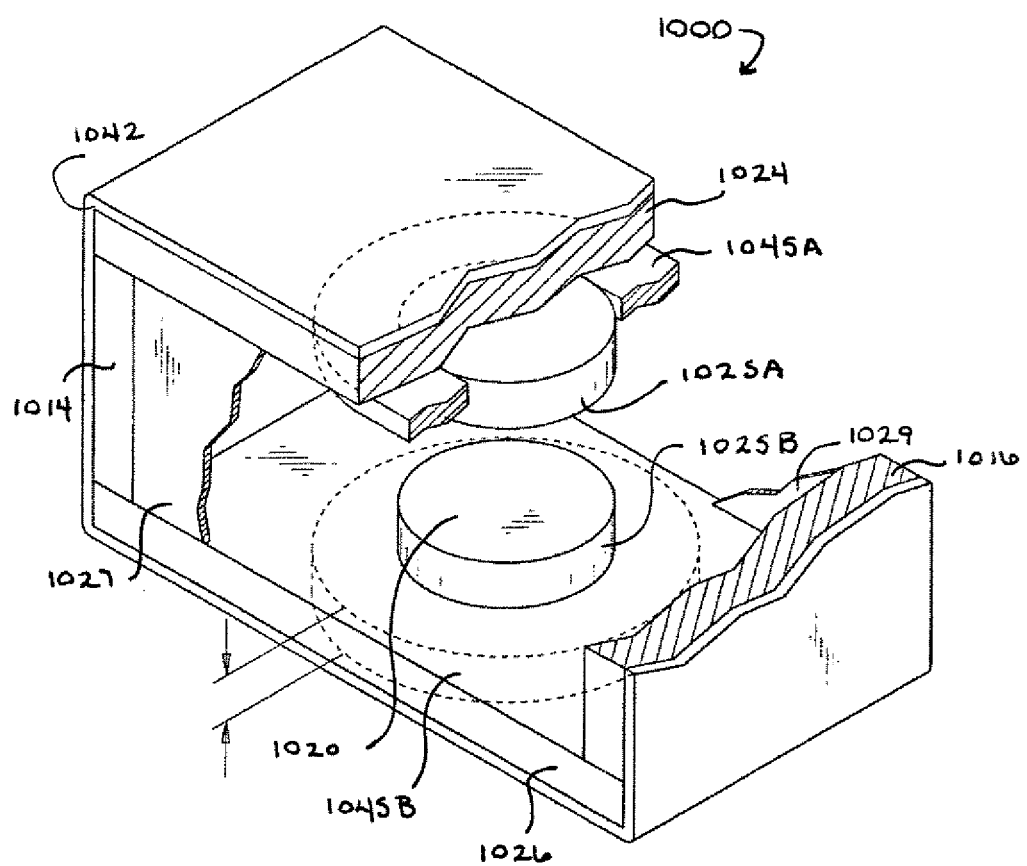
FIG. 10 shows an exemplary embodiment of the MRI apparatus of the present invention.
Figure 11:
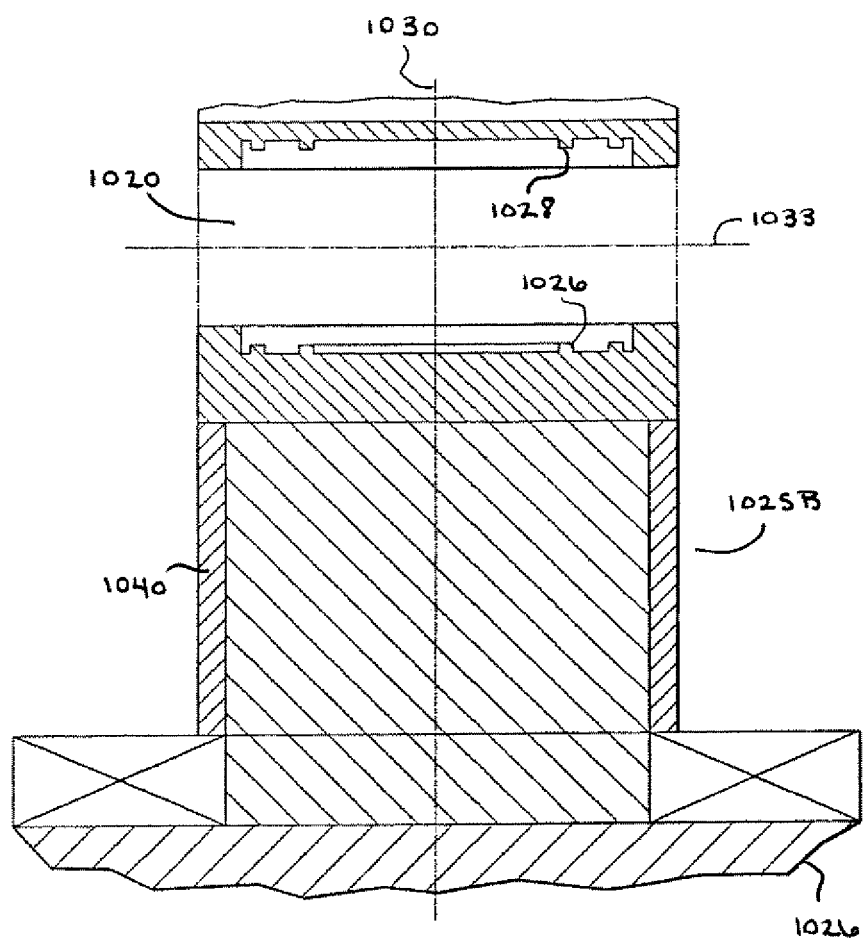
FIG. 11 shows an alternate view of the exemplary embodiment of FIG. 10.

With reference now to FIGS. 10 and 11, there is shown an apparatus in accordance with another preferred embodiment of the invention, including a frame 1000 having pole supports 1024 and 1026 and connecting elements 1014 and 1016 similar to those discussed above. The frame includes upper and lower poles 1025A and 1025B, which are generally cylindrical, and about 48 inches in diameter. The distance between pole tips and hence the dimension of gap 1020 in the axial direction along polar axis 1030 desirably is about 36 inches. Here the ratio of the shortest dimension of the pole tips transverse to the polar axis 1030 (the diameters of the pole tip) to the axial dimension of the gap distance is about 1.75:1. As discussed above with reference to FIG. 4, this ratio desirably is between about 1:1 and about 2:1.

With respect now to FIG. 11, lower pole includes a ferromagnetic stem extending from the lower pole support 1026 and a ferromagnetic tip element at the distal end of the pole, remote from the pole support 1026. Tip element is provided with annular ridges 1026 at various radial distances r from the polar axis 1030. In the arrangement shown, one such ridge is disposed at the outer edge of the pole tip. The upper pole tip is provided with matching annular ridges 1028. The ridges 1026 and 1028 effectively reduce the axial distance across gap 1020. Thus, the ridge shapes of the pole surface alter the reluctance at preferred geometric locations. The pattern of these different reluctances is selected to enhance the uniformity of the field in gap 1020. This allows use of a smaller ratio of pole diameter to gap size than would otherwise be required to achieve the same field uniformity. Other structural elements which provide differing reluctances at different locations relative to the polar axis 1030 can be employed. For example, the pole stems or pole tips may have internal gaps filled with non-ferromagnetic material to provide increased reluctance at some locations.

Optionally, pole 1025B may include a set of bucking elements 1040 encircling the pole stem between coil 1045B and the pole tip. The upper pole 1025A may include a similar set of bucking elements (not shown). Coils 1045A and 1045B are energized to direct flux in a forward direction along the poles 1025A and 1025B, so that the flux process in the forward direction through gap 1020. Bucking elements 1040 include permanent magnets arranged to direct flux in a rearward direction, opposite to the forward flux direction. For example, coils 1045A and 1045B may be activated to direct flux downwardly out of upper pole 1025A and into lower pole 1025B, through gap 1020, so that the forward direction is the downward direction. The bucking elements 1040 are arranged to direct flux into pole 1025A and out of pole 1025B, in the rearward or upward direction. This arrangement tends to confine the flux from the coils 1045A and 1045B within the poles 1025A and 1025B and tends to minimize leakage of flux from the peripheral surfaces of the poles 1025A and 1025B. This tends to promote a substantially unidirectional, uniform magnetic field within the region of the gap 1020 adjacent the polar axis 1030 and adjacent the medial plane 1033, midway between the pole ends.

The ferromagnetic frame also may include ferromagnetic walls 1027 and 1029 extending between the pole supports 1024 and 1026 on the long edges of the pole supports 1024 and 1026, i.e., on the edges of the pole supports 1024 and 1026 which are not occupied by the connecting elements 1014 and 1016. Thus, the pole supports 1024 and 1026 form two opposing sides of a hollow rectangular solid; the connecting elements 1014 and 1016 form two other opposing sides or wall elements and walls 1027 and 1029 form the remaining opposing sides or wall elements. Walls 1027 and 1029 desirably have openings (not shown) formed therein to provide access by a patient and an attendant to the interior of the frame. Walls 1027 and 1029 may be relatively thin metallic structures. These additional walls minimize leakage flux from the exterior of the frame. Conversely, these additional walls block the effects of varying magnetic fields outside of the frame on the field between the poles 1025A and 1025B, and thus provide a more uniform, stable field. Also, walls 1027 and 1029 form electrically conductive elements of a Faraday shield to minimize RF interference with the MRI imaging procedure.

In another preferred embodiment of the apparatus of the present invention, the frame may be provided with a layer or shell of bucking flux elements 1042 overlying the ferromagnetic elements of the frame on the outside of the frame. The bucking flux elements 1042 are permanent magnets arranged to direct flux along the exterior of the frame in a direction opposite to the direction of the flux induced by coils 1045A and 1045B.

Figure 12:
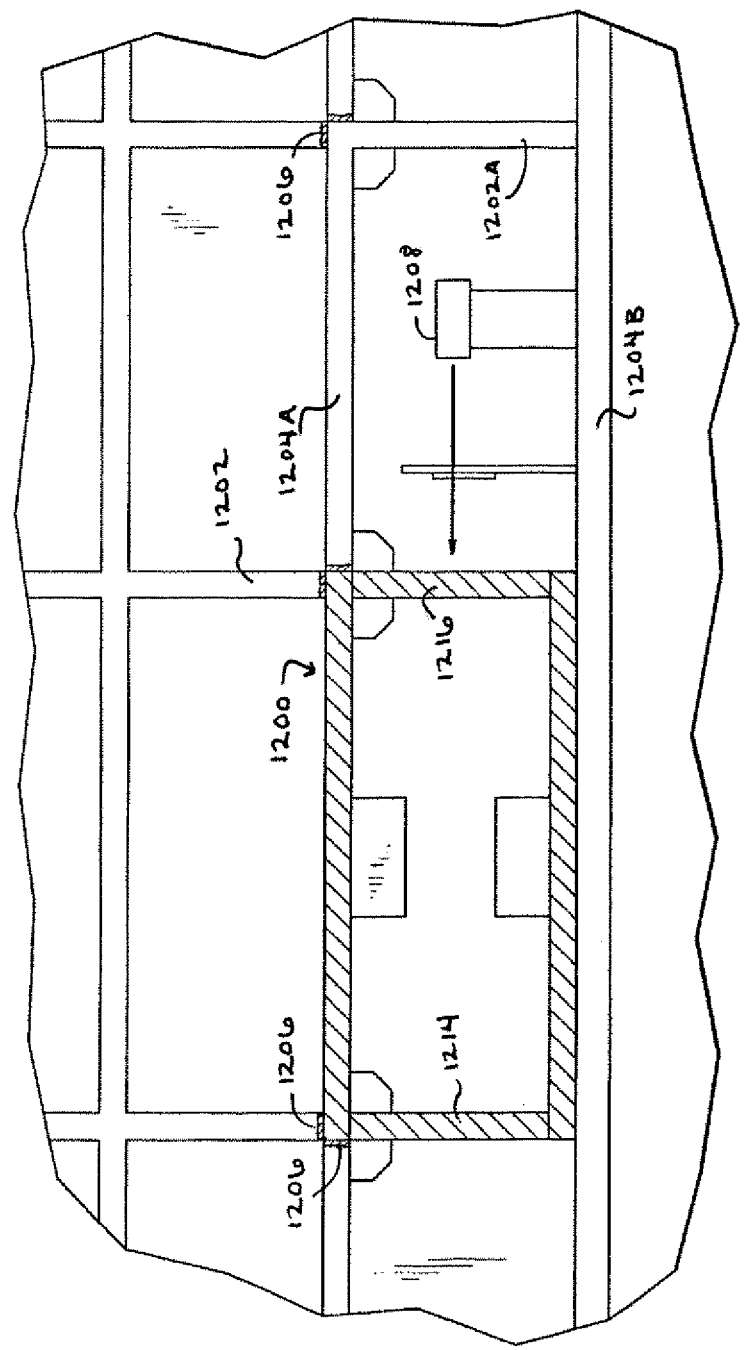
FIG. 12 shows an exemplary embodiment of the MRI apparatus of the present invention.

With reference now to FIG. 12, the magnet frame is illustrated as integrated within the structure of a building. For example, the connecting elements 1214 and 1216 of a magnet frame as discussed above may support other structural elements, such as columns 1202 and beams 1204. Where the beams 1204 and columns 1202 are ferromagnetic, such as in conventional steel frame construction, blocking plates 1206 framed from a diamagnetic material may be interposed between the frame of the MRI magnet and the remainder of the building frame to prevent transmission of magnetic flux therebetween. This minimizes any effect of induced magnetic fields in the remainder of the building frame on the MRI imaging procedure. Alternatively, other parts of the building frame may be integrated in the magnetic circuit of the magnet frame. Thus, beam 1204A, column 1202A, and beam 1204B are connected in magnetic circuit in parallel with connecting element 1216 and carry part of the magnetic flux. These elements may be isolated from other parts of the building frame by further blocking elements 1206.

Those elements of the building frame connected in the magnetic circuit may be protected from induced magnetic fields by appropriate shielding or otherwise may be located in areas of the building remote from sources of interfering magnetic field as, for example, areas remote from heavy electrical generating equipment and vehicular traffic. As also shown in FIG. 10, elements of the ferromagnetic frame may provide shielding for ionizing radiation such as x-rays or gamma rays used in therapeutic procedures. Thus, the ferromagnetic frame may be located adjacent a MRI operating room housing an x-ray or gamma ray treatment unit 1208, and the treatment unit may be arranged to direct radiation towards the ferromagnetic frame. Connecting element 1216 serves as a shielding wall. Alternatively or additionally, radiation-generating equipment may be disposed inside of the ferromagnetic frame, and hence inside of the room surrounded by the frame. Using these approaches, the cost of installing the ferromagnetic frame can be offset in part by cost savings achieved by eliminating other shielding structures which ordinarily would be provided in a hospital setting for the gamma ray or x-ray devices.

Figure 13:
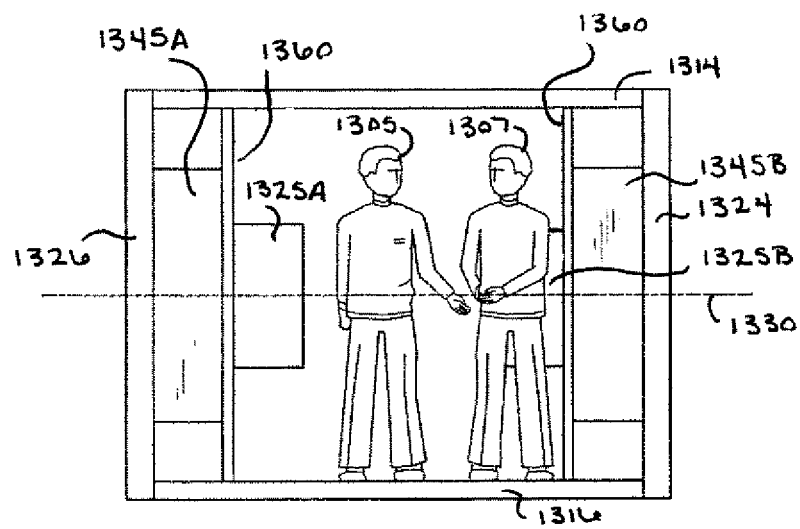
FIG. 13 shows an exemplary embodiment of the MRI apparatus of the present invention.

As shown in FIG. 13, a magnet in accordance with a further embodiment of the invention has a polar axis 1330 oriented generally horizontally, and has vertically oriented pole supports 1324 and 1326. Poles 1325A and 1325B project horizontally inwardly from the pole supports 1324 and 1326. The connecting elements 1314 and 1316 extend substantially horizontally. In the arrangement illustrated, coils 1345A and 1345B encircle the poles and are disposed in generally vertical planes adjacent the pole supports 1324 and 1326. Here again, the apparatus defines an operative space sufficient to accommodate a normal human attendant 1307. Once again, concealment structures such as false walls 1360 may be disposed inside of the magnet frame to conceal the magnet frame from a patient. The patient 1305 has the visual impression of entering a room where the poles 1325A and 1325B protrude from opposing walls of the room, rather than from the floor and ceiling. Alternatively, the coils 1345A and 1345B, and walls 1360 can be moved closer to the pole tips in this configuration. Apparatus with horizontally-projecting poles can be used, for example, to image a patient 1305 while the patient 1305 remains in a generally vertical orientation as, for example, in a standing position or a position close to the standing position. The same apparatus can also be used to form an image of the patient 1305 while the patient 1305 is in a seated or reclining posture, or in essentially any other position desired. This offers considerable benefits in diagnosing and treating conditions which vary with the patient's posture as, for example, certain orthopedic conditions. Here again, the large space within the magnet frame allows the attendant 1307 to have free access to the patient 1305 while the patient 1305 is being imaged.

Figure 14:
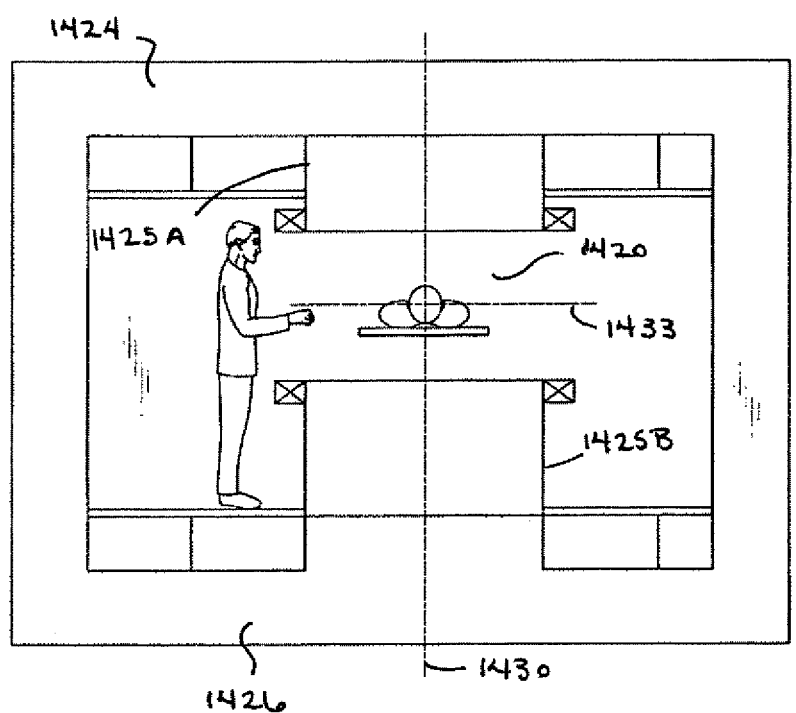
FIG. 14 shows an exemplary embodiment of the MRI apparatus of the present invention.

As shown in FIG. 14, a magnet in accordance with a further embodiment of the invention has poles of different lengths in the axis direction. Thus, the upper pole 1425A is shorter than the lower pole 1425B in the axial direction, along the polar axis 1430. Therefore, the medial plane 1433 of the gap 1420 is closer to the upper pole support 1424 than to the lower pole support 1426. The opposite arrangement, wherein the lower pole 1425B is shorter and the medial plane 1433 is closer to the lower pole support 1426 can also be used. Thus, by selection of appropriate pole lengths, the medial plane 1433 of the gap 1420 can be disposed at any desired elevation to facilitate positioning of the patient at a convenient height for the physician while still maintaining the area of interest of the patient in the region adjacent the medial plane 1433 of the gap 1420, where image quality is optimized. In magnets using unequal-length poles, additional flux-shaping devices such as auxiliary coils, auxiliary magnets and/or shaped pole tips preferably are provided to maintain flux uniformity. In an extreme case, one of the projecting poles may be eliminated entirely, so that the gap is defined between the tip of a single projecting pole and a polar region on the face of the opposite pole support. Thus, the plate constituting the pole support serves as the pole as well. In such an arrangement, the flux-generating winding may extend around the polar region and on the surface of the pole support plate. The asymmetry of this extreme arrangement typically requires use of features such as compensating shapes on the pole tip and/or on the polar region itself, and auxiliary shim coils. The principal energizing coils of the magnet may also be asymmetric to provide additional compensation.

Figure 15:
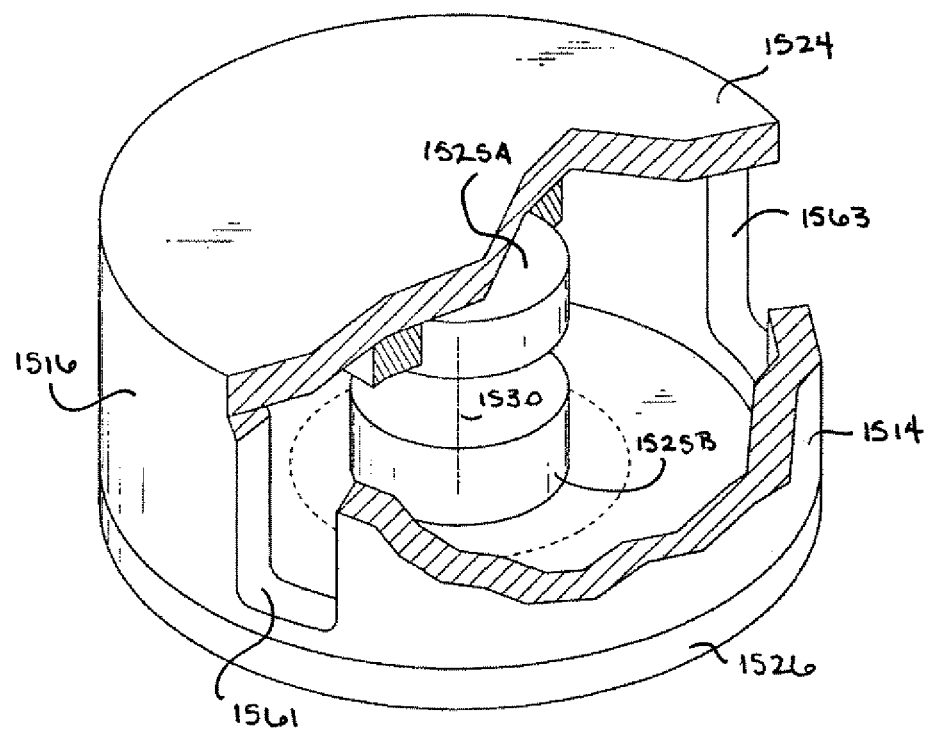
FIG. 15 shows an exemplary embodiment of the MRI apparatus of the present invention.

With respect now to FIG. 15, a magnet in accordance with yet another preferred embodiment of the invention incorporates a generally cylindrical ferromagnetic frame. Thus, the connecting elements 1514 and 1516 are generally in the form of sectors of a cylinder or other body of revolution coaxial with the polar axis 1530. A pair of openings 1561 and 1563 are provided on opposite sides of the polar axis 1530 for ingress and egress of patients and medical personnel. The upper and lower pole supports 1524 and 1526 are in the form of circular plates. In this particular embodiment, the poles 1525A and 1525B are cylindrical. However, elongated, non-circular poles, such as the rectangular poles discussed above can be employed in this embodiment as well. The operative space within the frame is in the form of an annulus encircling the poles and concentric with the polar axis.

Figure 16:
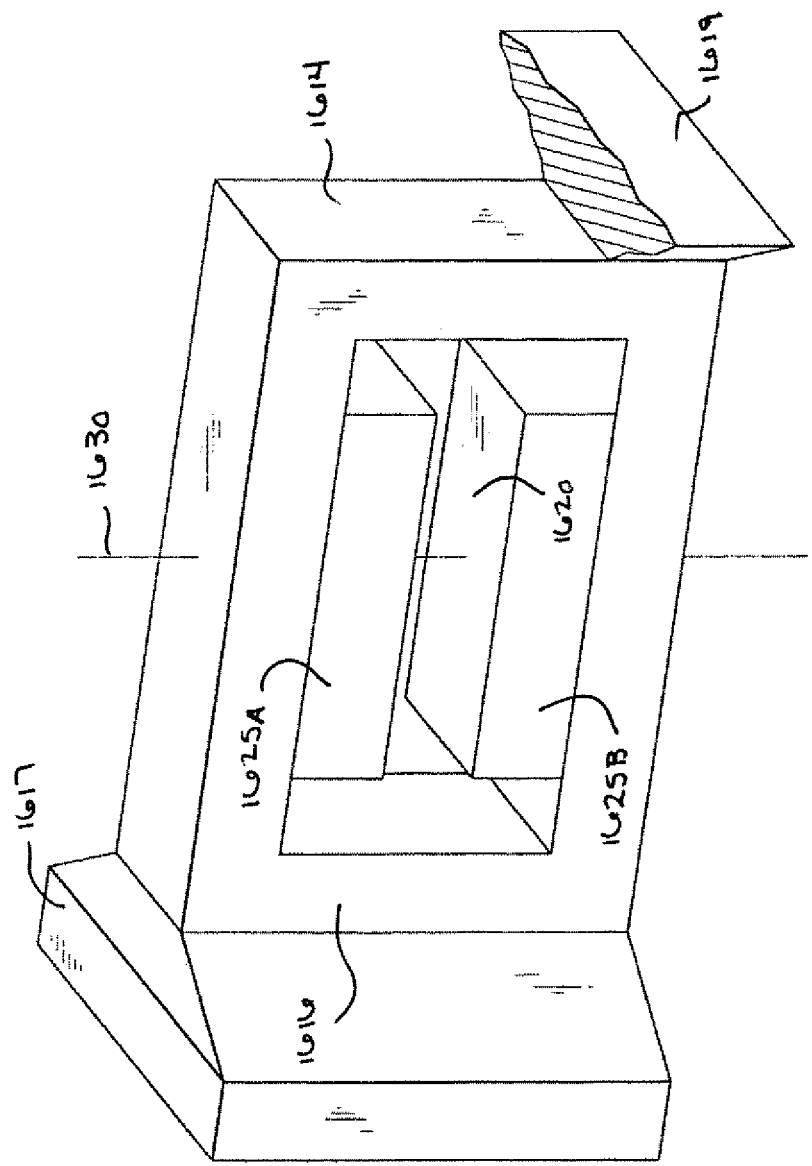
FIG. 16 shows an exemplary embodiment of the MRI apparatus of the present invention.

With respect now to FIG. 16, a magnet has a generally flat frame. That is, the widthwise dimensions of connecting elements 1614 and 1616 are not substantially larger than the corresponding widthwise dimensions of poles 1625A and 1625B. Preferably, the widthwise dimensions of the connecting elements 1614 and 1616 in this embodiment are about 48 inches or less at least in those regions of the connecting elements 1614 and 1616 closest to the gap 1620. The regions of connecting elements 1614 and 1616 remote from gap 1620 can be of essentially any dimensions. Thus, as depicted in FIG. 18, connecting element 1616 includes an outwardly flowing portion 1617 remote from the gap 1620 and connecting element 1614 includes a similar broad portion 1619 also remote from the gap 1620. These broad portions are optional.

Desirably, the distance between the interior surfaces of connecting elements 1614 and 1616 along a lengthwise dimension transverse to the polar axis and transverse to the widthwise dimensions is at least about 7 feet and most preferably between about 7 feet and about 14 feet. Poles 1625A and 1625B are elongated. The long dimensions of the poles 1625A and 1625B extend in the direction, from one connecting element 1614 to the opposite connecting element 1616. In this arrangement, the frame may not define an operative space inside the frame itself sufficient to accommodate a physician or other person. For example, the edges of pole 1625B may lie close to the interior surfaces of the connecting elements 1614 and 1616 that a person cannot enter between the pole and the connecting elements. However, because those portions of the connecting elements lying close to the gap have a relatively short widthwise dimension q, a person standing outside of the frame, but alongside the frame next to the pole, can still have reasonable access to the patient disposed in gap 1620. As in the embodiments discussed above, the elongated poles 1625A and 1625B provide an elongated region of uniform magnetic field for imaging. The flux source is not depicted in FIG. 16. The flux source may be disposed at any location where it does not impede access. For example, the flux source may include permanent magnets incorporated into the frame. Alternatively, coils may extend around the connecting elements 1614 and 1616 or the poles 1625A and 1625B. If the coils extend around the connecting elements 1614 and 1616, then the distance between the connecting elements 1614 and 1616 desirably is increased to compensate for the space occupied by the coil, so that the clear span between the interior faces of the coils is at least about 7 feet and desirably between 7 feet and 14 feet.

With reference again to FIGS. 4 and 5, a computer, not shown, is preferably located outside of the room 410, in order to keep the room 410 free of non-essential surgical equipment and otherwise protect it from strong radiation that could be harmful to the electronics therein. Alternatively, the computer may be located inside of the room 410, for ease of programming and control of the MRI during surgery. Indeed, the improved configuration and structure of room 410 pursuant to the teachings of the present invention make the inclusion of any and all equipment deemed necessary to a normally-functioning operating room possible.

The computer, which processes the raw received data into useful visual images, also controls the MRI apparatus, using commands received from the I/O interface, designated generally by the reference numeral 492, e.g., a keyboard, by sending appropriate signals and currents to the gradient coils 445A and 445B and the RF antennas 454, and receiving information from the RF transceivers 454. Using standard Fast Fourier Transformation (FFT) and Discrete Fourier Transformation (DFT) analysis, the data received from the MRI apparatus is translated into visual images, as is known in the art.

Figure 17:
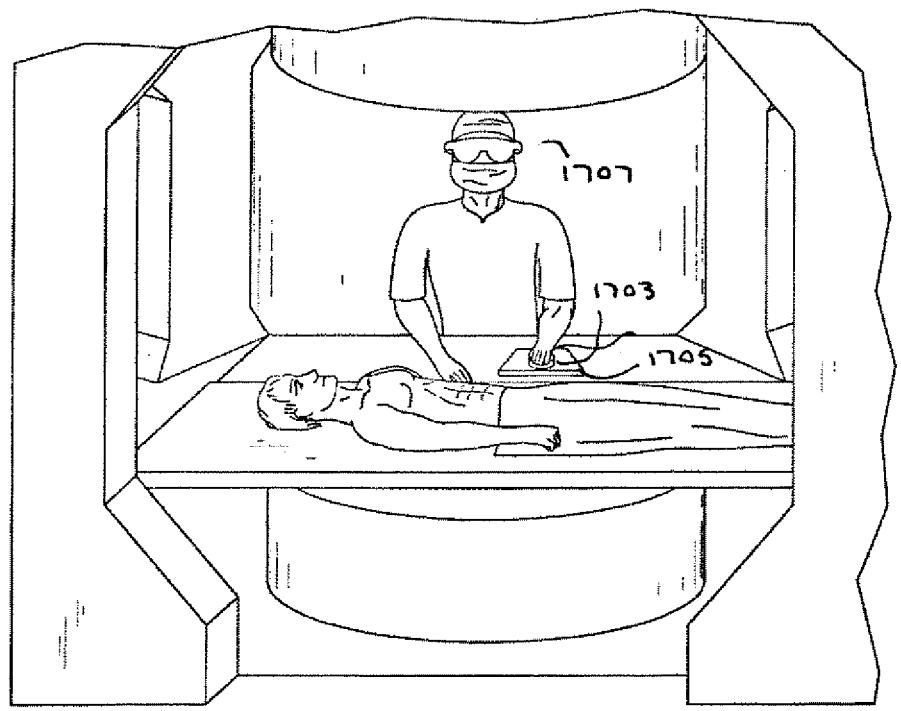
FIG. 17 shows an exemplary embodiment of the MRI apparatus of the present invention.

With respect now to FIG. 17, a mouse 1703 and a mouse pad 1705 are employed. Thus, the user interface of the MRI imaging system may incorporate a graphical user interface, wherein the user positions a cursor over a box or button appearing in the visual display and then actuates a button on the mouse to instruct the system to perform a particular action. The graphical user interface display may be shown in the same video goggles 1707 as used to display the MRI image. The mouse 1705 and graphical user interface may also be employed with a video display, such as with a projection display as discussed above with reference to FIGS. 4 and 5. The same mouse 1705 may be used to control a surgical robot including a surgical probe, needle or catheter. Also, both the option of the mouse control and the display options such as video goggles 1707 and projection are usable with other magnet frames, apart from those discussed above. Alternatively, an alternate device may be used to control the MRI, such as a joystick, trackball, or touch-screen. An example of an alternate device is found in Applicant's patent application Ser. No. 10/199,697, which is incorporated by reference herein.

The mouse 1703 or other device controls the MRI, by changing, for instance, the pulse sequence used in the MRI scan. A new pulse sequence may be used that facilitates a more efficient MRI scanning. The pulse sequence may be designed to more effectively utilize a specific scanning technique, such as Ti-weighted, T2-weighted, or balanced Ti- and T2-weighted scanning, as are already well-known in the art, as well as other and more sophisticated pulse sequences. The pulse sequence may also be designed to more effectively utilize any scanning technique, such as by increasing the overall signal-to-noise ratio or by requiring less power. A description of such an MRI controller is shown in Applicant's Assignee's application Ser. No. 10/236,909, which is incorporated by reference herein. A pulse sequence used specifically in MRI scanning is the Bessel function, shown in Applicant's Assignee's application Ser. No. 10/314,999, which is incorporated by reference herein.

The visual images generated by the computer may be displayed on a single monitor or multiple monitors, designated generally by the reference numeral 490, inside the room 410, so that the visual information is immediately available to the physicians, technicians, nurses, and others. The visual images may be duplicatively displayed on an additional monitor located near the computer and I/O interface 492, when the computer and I/O interface 492 are located outside of the room 410, so that the physician or technician monitoring and controlling the MRI may also view the images produced. Alternatively, the visual images may be displayed on another medium, such as a headset displaying the images for the physicians, technicians, or nurses as an overlay or superimposed on the patient 405. Further details on virtual reality and other simulated environments for use in the present invention are set forth, for example, in U.S. Pat. No. 6,208,145, which is incorporated by reference herein.

As depicted in FIG. 17, a further embodiment of the invention utilizes video display goggles 1707 connected to the magnetic resonance imaging unit to provide a visible display of the MRI image to the physician. The video display goggles 1707 may be arranged to display the image in front of the physician's eyes upon command. At other times, the video display goggles 1707 provide a clear vision so that the physician can see the patient in the normal manner. Alternatively, the video display goggles 1707 may be arranged to provide the MRI image superposed on the normal field of view so that the physician can observe both the MRI image and the patient simultaneously. Such superposition can be achieved, for example, using the superposition methods commonly employed in "heads up display" technology. Alternatively, the video goggles may be adapted to provide the MRI image in a corner of the visual field, so that the physician can see the image by turning his or her eyes in a particular direction as, for example, by rolling his or her eyes, away from the patient.

The images displayed on the monitor or monitors, or other display device such as a headset, are dynamic and substantially real-time. It should be understood that "real-time" refers to a rate of frames per second, rather than "true" real-time video imaging. Indeed, true real time images would be of great benefit to surgeon performing a procedure within an MRI operating room. The resolution and amount of processing can be controlled to give a frame rate that could approximate real time. the quality of the image may be somewhat procedure specific. Some procedures may require only a rudimentary image to approach real time viewing, such as positional location of a probe.

In minimally-invasive surgery, the tiny incision (for the catheter or probe) as opposed to major surgery, makes treatment far less life-threatening. A feature of the present invention which is critical to carrying out MRI-guided surgery is the provision of surgical instruments that can deviate from a linear path of travel through the human body while under MRI guidance. A preferred embodiment of such an instrument is shown in FIGS. 18A-18D.

Figure 18A:
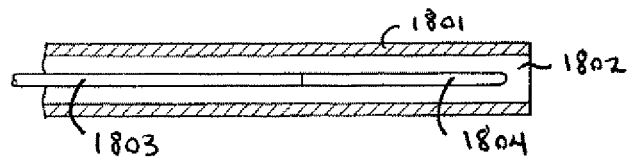
FIGS. 18A-18D show exemplary illustrations of the catheters used in the present invention.

A catheter and guide combination 1800 shown in FIG. 18A is comprised of a tubular catheter body 1801 having an open end 1802. The open end 1802 constitutes the leading end of the catheter body 1801 which is inserted into the body of a patient. A guide wire 1803 extends through the tubular catheter 1801 along its length and is movable lengthwise through the catheter 1801. The guide wire 1803 terminates at a movable end portion 1804 which is described below. The movable end portion 1804 is the leading end of the guide wire 1803 when it is advanced into the body of a patient.

The use of the catheter and guide structure is shown by the sequence of FIGS. 18A-18D. Initially the catheter 1801 and guide wire 1803 are straight. They are inserted into the patient's body as a pair and advanced together with the catheter open end 1802 and the guide wire end portion 1804 advancing together as the leading ends of the structure.

Figure 18B:
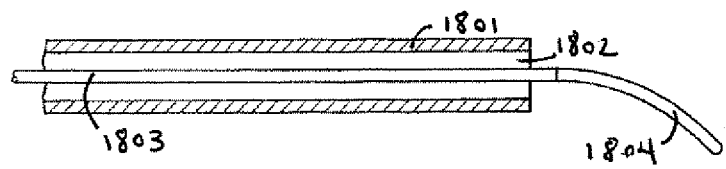

When it is desired to change the direction of advance of the catheter and guide wire the advancing of the catheter 1801 is stopped while the guide wire 1803 is advanced so that the guide wire end 1804 extends beyond the open end 1802 of the catheter 1801. The end 1804 of the guide wire 1803 is caused to deflect toward the intended new direction of advance. This condition is shown in FIG. 18B.

Figure 18C:
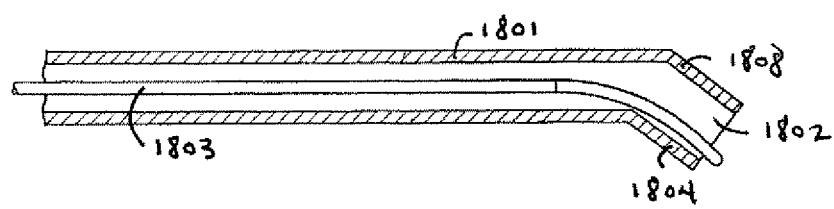

Advancement of the catheter 1801 is then resumed with the open end 1802 of the catheter following along the curved end portion 1804 of the guide wire 1803. The deflected end portion 1804 causes the advancing catheter 1801 to change direction as it advances with a result that a bent portion 1808 is induced in the normally straight catheter 1801. This condition is shown in FIG. 18C.

Figure 18D:
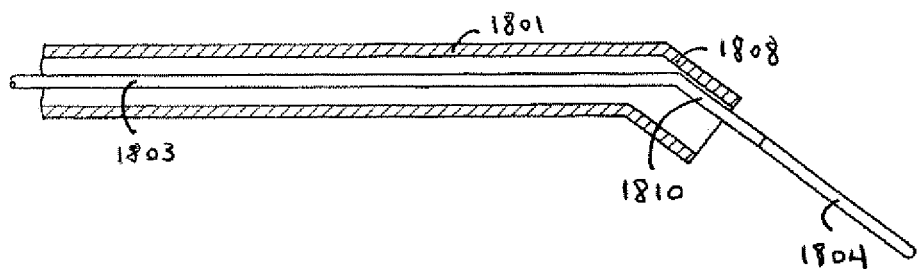

Next, the guide wire 1803 is advanced in the new direction. The catheter 1801 is surrounded by body tissue so that the bend 1808 will not relax and straighten, even after the end portion 1804 of the guide wire is advanced out through the open end 1802 of the catheter 1801. Consequently, as the guide wire 1803 is advanced into the patient's body it will change direction at a bend 1810 which is a result of the guide wire advancing against the bent portion 1808 of the catheter 1801. This is shown in FIG. 18D.

If the tissue surrounding the catheter is sufficiently firm, the catheter can be advanced along with the guide wire without losing the change of direction achieved by the bent portion 1808 of the catheter 1801. Both the catheter 1801 and the guide wire 1803 should be resilient so that they can be bent, and so they will also return to their relaxed shape after any bending pressure has been removed. They must likewise be sufficiently stiff to allow them to be advanced axially by pushing on them at a location remote from the advancing end. Finally, the guide wire 1803 should be nonferrous to avoid image artifacts caused by magnetic field homogeneity.

Figure 19:
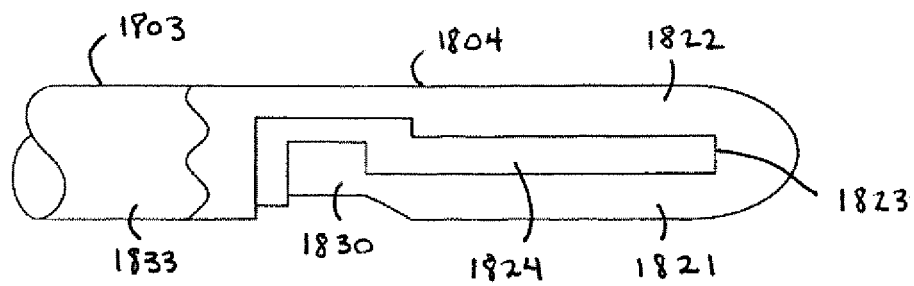
FIG. 19 show an alternate view of the catheters of FIGS. 18A-18D.

Details of the movable end portion 1804 of the guide wire 1803 are shown in FIG. 19. The movable end portion 1804 is shown in longitudinal section and is comprised of a bimetallic structure having a lower 1821 and an upper half 1822. Lower half 1821 and upper half 1822 are each made from a different metal having a different coefficient of thermal expansion. The halves 1821, 1822 meet at a permanent junction 1823 at the free end of the movable end portion 1804.

A thin insulative layer 224 is disposed between the metal halves 1821 and 1822 of the movable end 1804, except at the junction 1823. For purposes of illustration the insulative layer 1824 is shown thicker than it would be made in practice. The guide wire 1803 is comprised of a coaxial conductor for providing a current path to the movable end 1804. The center conductor 1830 of the guide wire is fused to the bottom half 1821 of the movable end portion. An inner insulator 1831 connects with the insulative layer 1824 and also serves to insulate the center conductor 1830 of the guide wire from the outer conductor 1832. The upper half 1822 of the movable end is fused to the outer conductor 1832 of the guide wire, and the guide wire is covered by an outer insulative layer 1833.

The structure of the movable end portion 1804 of the guide wire 1803 results in a series circuit for flowing current through the bimetal structure of the movable end portion 1804. In particular, current flows through the center conductor 1830 of the guide wire into the lower half 1821 of the movable end portion and through the junction 1823. The current continues through the upper half 1822 of the movable end portion and back through the outer conductor 1832 of the guide wire. The insulative layer 1824 insures that current flows through the entire length of the bimetallic structure of the movable end portion for heating the two metal halves 1821, 1822 and maximizing the deflection which will occur because of their different respective thermal coefficients of expansion.

Figure 20A:
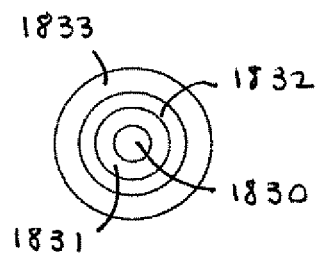
FIGS. 20A-20D shows an alternate view of the catheters used in the present invention.
Figure 20B:
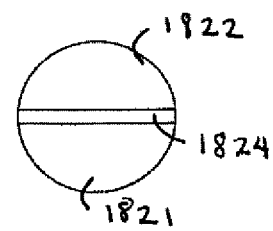
Figure 20C:
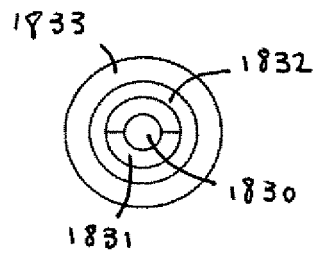
Figure 20D:
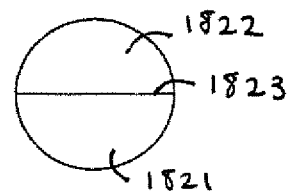

The cross-sectional structure of the movable end portion along the successive section lines in FIG. 19 is illustrated in FIGS. 20A-20D. FIG. 20A shows the concentric structure of the guide wire comprising the central conductor 1830 and the outer coaxial conductor 1832 with the intermediate insulating layer 1831 between them. FIG. 20B shows the cross-sectional structure at the junction between the movable end 1804 and the guide wire 1803. FIG. 20C is a cross section through the movable end portion 1804 and shows the position of the insulative layer 1824 between the metallic halves 1821 and 1822. Finally, FIG. 20D is a cross section through the junction 1823 of the two metal halves 1821 and 1822.

Figure 21:
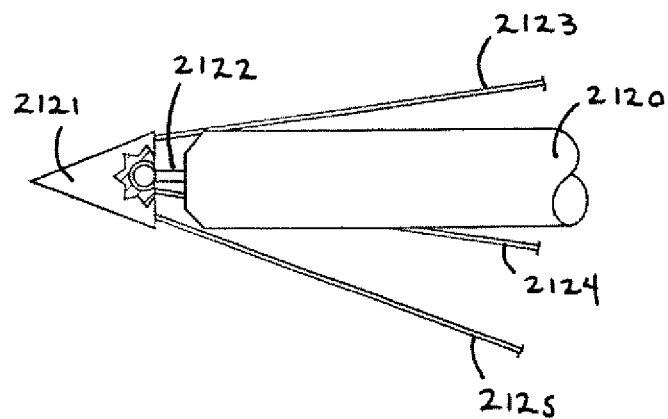
FIG. 21 shows an exemplary illustration of the catheter used in the present invention.

Another embodiment of the guided instrument according to the invention is shown in FIG. 21. The instrument is comprised of a guide wire 2120 having a conical head 2121 mounted on one end of the guide wire. A pivot 2122 mounts the head 2121 for pivotal movement relative to the longitudinal axis of the guide wire 2120. A plurality of control wires 2123, 2124 and 2125 are disposed around the periphery of the head 2121. Applying tension to one or more of the guide wires 2123-2125 is effective to pivot the head 2121 on the pivot 2122. Selective application of tension to different control wires allows the head 2121 to be oriented in a controllable fashion. The illustrative embodiment has three control wires 2123-2125, but the number of control wires could be increased. The illustrative embodiment can be used with a catheter as in the previously described embodiment, or the catheter can be dispensed with. Surrounding tissue will be effective to hold the control wires 2123-2125 next to the guide wire 2120 as the instrument advances through the tissue of a patient.

Figure 22A:
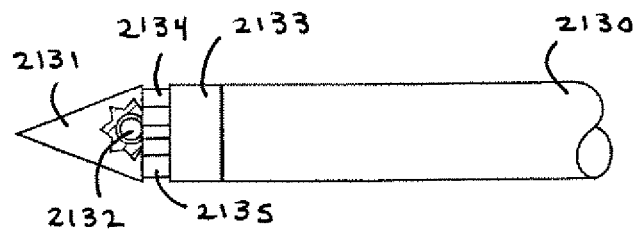
FIGS. 22A and 22B show exemplary illustrations of the catheters used in the present invention.
Figure 22B:
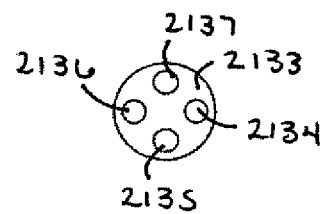

Another embodiment of the instrument according to the invention is shown in FIGS. 22A and 22B. The guide wire 2130 has at one end thereof a head 2131 mounted by a pivot 2132 on a base 2133. The base 2133 is fixed to the guide wire 2130. A plurality of piezoelectric actuators 2134, 2135, 2136 and 2137 are disposed around the circumference of the base 2133 and between the base 2133 and the head 2131. The layout of the piezoelectric actuators is shown in FIG. 22B.

By applying voltages to different actuators the orientation of the head 2131 is varied in a pivotal motion relative to the longitudinal axis of the guide wire 2130. Conductive paths extending through the guide wire 2130 can provide individual voltages to the respective piezoelectric actuators to allow them to be energized independently. This embodiment of the invention is particularly advantageous because the actuating signal, an electrical voltage, can be set to a very high degree of precision and the resulting displacement of the head 2131 relative to the guide wire 2130 can be determined very precisely.

In a preferred embodiment, the instrument according to the invention includes a material which will give a strong MRI signal so that the instrument will appear prominently in magnetic resonance images. The instrument could comprise a tip which is paramagnetic, or alternatively the instrument tip could be opaque to MRI. The position of the instrument in a magnetic resonance image of the instrument and surrounding anatomy will appear correct relative to the surrounding anatomy. The instrument within a small region of interest or field of view can advantageously be imaged more frequently than the entire anatomy of interest, and the instrument image can be updated more frequently, to allow the instrument motion to be tracked by MRI.

The display for displaying a magnetic resonance image of the anatomy to be treated can include means for receiving a representation of the path to be followed by the instrument. The means for receiving a path representation can include a cathode ray tube for displaying the magnetic resonance image together with a light pen system which will allow the intended instrument path to be drawn on the displayed image. The advance of the instrument during the course of treatment is displayed to allow comparison between the planned and actual instrument path, and correction or adjustment of the instrument path as needed.

The catheter and guide wire previously described can be used for carrying out various methods according to the present invention. The catheter and guide wire combination are advanced through a patient to a treatment site in the manner previously established. The guide wire is then withdrawn leaving the catheter in place, and any of a variety of treatments using the catheter can be commenced.

As is known in the art, the MRI apparatus 300 can be used to produce T1-weighted imaging, T2-weighted imaging, T2* weighted imaging, and proton-density weighted imaging, as desired for the particular surgical technique. In the brain, for example, T1-weighting causes fiber tracts, i.e., nerve connections, to appear white, congregations of neurons to appear gray, and cerebrospinal fluid to appear dark. However, the contrast of "white matter," "gray matter" and "cerebrospinal fluid" is reversed using T2 and T2* imaging. When imaging lesions, they appear dark in T1-weighted imaging and white in T2-weighted imaging. Proton density-weighted imaging provides little contrast in normal subjects.

After comparison with the prior art, represented by FIGS. 1 and 2 herein, the present configuration is unlike all previous designs in that doctors and technicians can easily walk inside of the magnet instead of being inconvenienced by it. With reference again to FIG. 3, patient 305 on the table 315 is atop one of the two magnet poles 320 of the magnetic resonance device within a larger room 310 extending thereabout.

In particular, in the embodiment shown in FIG. 3, the surface 330 of the pole 320B is substantially flush with the floor 350, enabling the patient 305 and the table 315, as well as any equipment, easy movement across the floor 350 without obstructions. In view of this new design, an entire surgical team and equipment can now be positioned about the patient 305, with dynamic imaging, e.g., greatly facilitating usage by surgeons, anesthesiologists, nurses, and surgical support systems, including respirometers, heart pumps, cardiopulmonary bypass units, lithotriptors, surgical navigation systems, endoscopy systems, anesthesia carts, arthroscopy units, defibrillators, thermal regulation systems, fiberoptic lighting systems, and electrophysiology platforms such as electroencephalogram (EEG), electrocardiogram (EKG), and electromyogram (EMG) systems. Most importantly, all of these individuals and all of the attendant equipment in this configuration have total, full 360° access to the patient 305.

Using the MRI system and methodology of the present invention, a variety of minimally-invasive surgical techniques can be performed. Many surgical instruments are commercially available in MR-safe materials, which must be non-ferrous and non-magnetic. Typically, these materials are plastic, stainless steel, or other metal alloys. However, as some conductive metal alloys do not image properly, ideal MR-safe materials include carbon, plastics, and other low-conductivity metals, as is understood in the art.

In a preferred embodiment of the present invention, the open MRI operating room and methodologies are used to perform minimally-invasive surgery. Some examples of minimally-invasive intraoperative MRI surgery include arthroscopy, endoscopy, and laproscopy. Flexible instruments such as catheters, guidewires, and flexible endoscopes are advantageously used in conjunction with the present invention, enabling dynamic guidance through sensitive and delicate tissues using intraoperative MRI data. Markers, such as magnetic coils, can be attached to these instruments for imaging when inside the patient body.

In a preferred embodiment, the instrument according to the invention includes a material which will give a strong MRI signal so that the instrument will appear prominently in magnetic resonance images. The instrument could comprise a tip which is paramagnetic, or alternatively the instrument tip could be opaque to MRI. The position of the instrument in a magnetic resonance image of the instrument and surrounding anatomy will appear correct relative to the surrounding anatomy. The instrument within a small region of interest or field of view can advantageously be imaged more frequently than the entire anatomy of interest, and the instrument image can be updated more frequently, to allow the instrument motion to be tracked by MRI.

The catheter and guide wire previously described can be used for carrying out various methods according to the present invention. The catheter and guide wire combination are advanced through a patient to a treatment site in the manner previously established. The guide wire is then withdrawn leaving the catheter in place, and any of a variety of treatments using the catheter can be commenced.

The catheter can be used for the direct delivery of a therapeutic chemical to the treatment site. The treatment site can be a tumor, or a tissue containing a tumor, as well as a site where a surgical treatment is to be carried out. The therapeutic chemical can be delivered in an unactivated state, or as an active therapeutic chemical. Activation of the therapeutic chemical can be carried out in vivo by an appropriate means. For example, the therapeutic chemical may comprise a porphyrin such as protoporphyrin which can be activated in vivo by light. The therapeutic chemical is first introduced, for example, into a tumor, through the catheter, and then an optical fiber is extended through the catheter into the tumor for directing light to the protoporphyrin. High intensity laser light is delivered through the optical fiber to activate the protoporphyrin within the tumor.

Additionally, the patient 305 can be given an oral contrast agent, such as water, a paramagnetic contrast agent, e.g., a gadolinium compound, a superparamagnetic contrast agent, e.g., iron oxide nanoparticles, or other contrast agent. Alternatively, a contrast agent may be injected into a particular area of interest rather than taken orally.

Another important embodiment of the invention includes the delivery of a therapeutic chemical to a tissue containing a tumor. In particular, the introduction of antioxidants into the tissue, followed by continuous monitoring in the form of repetitive magnetic resonance imaging is used to evaluate the efficacy of the antioxidant. This method may be carried out with the further step of introducing the antioxidant directly into the tumor and simultaneously delivering a therapeutic chemical for treatment of the tumor directly into the tumor. Suitable antioxidants include a tocopherol (Vitamin E), butylated hydroxy toluene, and carotene.

Another method according to the invention is a method for identifying a treatment regimen. This is carried out by administering a therapeutic chemical directly to a tumor within a patient, and continuously monitoring the tumor by repetitive magnetic resonance imaging to determine the efficacy of the therapeutic chemical. Based on the determined efficacy the amount of therapeutic chemical administered is adjusted to improve the effectiveness of the treatment carried out with the therapeutic chemical.

The method just described can be augmented by administering a second therapeutic chemical, (and subsequent therapeutic chemicals), directly to the tumor within the patient after the efficacy of the first administered therapeutic chemical has been determined. The tumor is continuously monitored by repetitive magnetic resonance imaging after administration of the second (or subsequent) therapeutic chemical to determine the efficacy of the latter administered therapeutic chemical. The amount of the second therapeutic chemical is likewise adjusted based on the determined efficacy in order to improve the treatment.

A variation of the methods just described is carried out by administering a plurality of therapeutic chemicals directly to separate regions of the same tumor within a patient. The tumor is continuously monitored by repetitive magnetic resonance imaging after the administration of the therapeutic chemicals to determine the effectiveness of the treatment. Thereafter, the administered amounts of selected therapeutic chemicals are adjusted to improve the treatment. In another embodiment of this method, one or more of the administered therapeutic chemical are selected for ongoing treatment of the tumor.

In another embodiment, oxygen is delivered as a therapeutic chemical. The delivery of oxygen is also used for determining the degree of tissue oxygenation. The tissue is imaged and then oxygen is delivered to the tissue by direct perfusion with gaseous oxygen or by administering the oxygen in combination with an oxygen carrier molecule such as hemoglobin or heme. During and after the administration of oxygen the tissue is continuously imaged and the contrast of the images before and after administration is compared. The change in image contrast is a measure of the initial degree of oxygenation of the tissue.

Image contrast also provides a measure for determining the uptake of administered therapeutic chemicals, and the uniformity of distribution of a chemical within an organ or a particular target tissue. The ability to monitor the uptake of an administered therapeutic chemical permits the development of treatment regimens involving systemic delivery of the therapeutic chemical. Moreover, image contrast permits determination of a desired degree of tissue perfusion and allows correct dosage of a therapeutic chemical to be selected.

Where the target tissue to be treated is a tumor, a preferred embodiment of the invention includes imaging the tumor by three dimensional (3D) imaging. The invention is not limited to a particular type of tumor, but includes the treatment of hepatic, pancreatic, breast, colon, lung, brain, bone, prostate, ovarian, uterine, kidney, stomach, head, neck, testicular and neurological tissue tumors, and tumors in other tissue and organs. Moreover, the treatment method is not limited to the delivery of a therapeutic chemical, and the instrument according to the invention includes instruments having means for delivering various treatment agents including heat, light or radiation, as well as a therapeutic chemical. The instrument may also include means for excising tissue.

In the method according to the present invention, the surgical treatment is carried out under MRI guidance with instruments according to the invention in order to avoid the extensive cutting of tissue which occurs in conventional surgery. An advantage of MRI guidance is the freedom to view the region of anatomy where surgery is to be performed from an arbitrary orientation selected based on anatomical and procedural considerations. An additional advantage of MRI is its unique capability to provide full 3D visualization.

In another preferred embodiment, intraoperative MRI is used for localizing tissue abnormalities and determining apparent tumor margins. In particular, while some neurosurgery using intraoperative MRI has been performed under limited circumstances, the present invention allows intraoperative MRI surgery on other parts of the body, as well as the head and brain, with greater access than ever before. Intraoperative MRI may be used, e.g., to guide in biopsies in tumor resections, in the detection of pathological changes, in fully characterizing tissue damage, in the detection of subtle physiologic, metabolic, or structural changes, and to provide functional anatomic detail by evaluating parameters such as diffusion, perfusion, and/or flow.

In another preferred embodiment, the open MRI operating room and methodologies of the present invention are used in the treatment of tumors using chemotherapy. In current systemic chemotherapy treatments, the chemotherapy agent is taken orally, systemically treating the entire body. Indeed, when the chemotherapy agent is given by mouth, there is no way to certify that the agent actually reached the target organ or tissues. Also, there is no way to ascertain the dose level achieved within the target organ and for how long the required dose level was maintained within the tissue without being washed out. Because the agent is given by mouth, systemically, the actual dose the patient receives is often limited by the toxic side effects on the body's healthy tissues, in other words, consuming more toxic chemicals than absolutely needed.

When using an intraoperative surgery technique using the open MRI operating room of the present invention, a needle can be introduced directly into the tumor or tumors. In particular, the needle can be guided using intraoperative MRI data through a least-damaging route and deliver the toxic chemicals, at very high dose, directly into the tissue being treated. Monitoring the dosage and the tumor, as well as healthy tissue, using intraoperative MRI, has several beneficial effects, discussed in more detail hereinbelow.

A magnetic tag, such as gadolinium, injected with the agent will illustrate the perfusion of the agent on the MR image and enable the surgeons or post-operative teams to measure the rate of washout of the chemotherapy agent from the area of treatment. Also, tumor tissue dose levels can be continually monitored quantitatively by MR imaging of a gadolinium-enhanced tumor to determine the degree to which effective dose levels are being maintained within the tumor. Washout of the chemotherapeutic agent from the target tissue can be followed by studying changes in the image intensity of the magnetic tag with time. If the tag is bound to the treatment agent, then following the washout characteristics of the magnetic tag will directly correlate with those of the therapeutic agent. If the agent and tag are not bound together but merely constitute a mixture, then washout of the magnetic tag may lead or lag washout of the treatment agent. The actual relationship of the agent and tag during washout could be established experimentally, and would provide potentially valuable clinical information.

The dose, calculated from the number of cc's injected into the tumor, assures that the pharmaceutical agent has reached the tumor at the required dose level. Also, direct injection and exclusive delivery of the chemotherapeutic agent to the tumor circumvents the toxic effects of the agent on the body's other healthy organs and bypasses these toxicities that limit the dose that can be given to the patient when the chemotherapeutic agent is given by mouth. Because the direct injection of the dose limits the toxicity of systemic treatments, much higher doses of the chemotherapeutic agent are achievable within the tumor.

Once the needle or catheter has been successfully placed within or at the tumor, the needle itself can be replaced with a permanent indwelling catheter for facilitating the delivery of follow-up doses of the chemotherapy agent of other anti-tumor agents, e.g., angiogenesis inhibitors, immunotherapy agents, etc., to certify by post-operative MR imaging that effective dose levels of the anti-tumor agent are being achieved within the tumor and maintained throughout the course of the therapy.

In a preferred embodiment of the present invention, such as illustrated in FIGS. 3 and 4, a method for guided surgery using magnetic resonance imaging includes conducting surgery on a patient in an operating room and directly guiding the surgery on the patient in the operating room using intraoperative magnetic resonance imaging, whereby the surgeon using the intraoperative magnetic resonance imaging minimizes trauma to the patient.

In another preferred embodiment of the present invention, a magnetic resonance device includes a magnetic resonance magnet, magnetic resonance flux lines of the magnet passing through an operating room and a patient positioned on a table therein; and a display device, the display device receiving intraoperative magnetic resonance imaging of a portion of the patient on the table, whereby a surgeon may directly guide surgery on the patient using the intraoperative magnetic resonance imaging and minimize trauma to the patient.

In a preferred embodiment of the present invention, a method for guided chemotherapy includes conducting a treatment on a patient in a treatment room, the treatment comprising insertion of a needle to a tissue of interest within the patient; and directly guiding the needle to the tissue of interest of the patient using intraoperative magnetic resonance imaging, whereby a health professional using the intraoperative magnetic resonance imaging targets treatment to the tissue of interest and minimizes trauma to the patient.

In another preferred embodiment of the present invention, a magnetic resonance device for guided chemotherapy includes a magnetic resonance magnet, magnetic resonance flux lines of the magnet passing through the treatment room and a portion of a patient positioned on a table therein; and a display device, the display device receiving intraoperative magnetic resonance imaging of the portion of the patient on the table, a health professional in the treatment room directly guiding a needle to a tissue of interest within the portion of the patient using the intraoperative magnetic resonance imaging, whereby treatment to the tissue of interest is targeted and trauma to the patient is minimized.

In a preferred embodiment of the present invention, a method for tracking the efficacy of a treatment includes conducting a treatment in a treatment room on a tissue of interest within a patient, the treatment including a magnetic tag for administration to the tissue of interest; directly guiding the treatment on the tissue of interest of the patient in the treatment room using intraoperative magnetic resonance imaging; and administering, after guidance of the treatment to the tissue of interest using the intraoperative magnetic imaging, the magnetic tag to the tissue of interest, whereby a health professional using the intraoperative magnetic resonance imaging minimizes trauma to the patient and whereby the efficacy of the treatment can be monitored by intraoperative magnetic resonance imaging of the magnetic tag.

In another preferred embodiment of the present invention, a magnetic resonance device includes a magnetic resonance magnet, magnetic resonance flux lines of the magnet passing through a treatment room and a portion of a patient positioned on a table therein for treatment, the treatment including a magnetic tag for administration to a tissue of interest; and a display device, the display device receiving intraoperative magnetic resonance imaging of a tissue of interest within the portion of the patient on the table and of the magnetic tag administered to the tissue of interest, whereby a health professional using the intraoperative magnetic resonance imaging minimizes trauma to the patient, and whereby the efficacy of the treatment can be monitored by intraoperative magnetic resonance imaging of the magnetic tag.

In a preferred embodiment of the present invention, a method for guided chemotherapy includes conducting a treatment on a patient in a treatment room; and directly guiding the treatment on the patient in the operating room using intraoperative magnetic resonance imaging, whereby a health professional using the intraoperative magnetic resonance imaging minimizes trauma to the patient.

In another preferred embodiment of the present invention, a magnetic resonance device includes a magnetic resonance magnet, magnetic resonance flux lines of the magnet passing through a treatment room and a patient positioned on a table therein; and a display device, the display device receiving intraoperative magnetic resonance imaging of a portion of the patient on the table, wherein a health professional directly guides treatment on the patient using the intraoperative magnetic resonance imaging, whereby trauma to the patient is minimized.

The foregoing description of the present invention provides illustration and description, but is not intended to be exhaustive or to limit the invention to the precise one disclosed. Modifications and variations are possible consistent with the above teachings or may be acquired from practice of the invention. Thus, it is noted that the scope of the invention is defined by the claims and their equivalents.

What is claimed is:

1. A magnetic resonance imaging room comprising:
   a plurality of walls, a floor and a ceiling, defining an MRI room space therein;
   a ferromagnetic shield, said ferromagnetic shield being within said plurality of walls, floor and ceiling to shield said MRI room space from outside interference and prevent outward interference;
   a magnet, the poles of said magnet positioned substantially along said floor and ceiling within said MRI room space, said poles having a gap therebetween where lines of flux flow therethrough;
   a patient positioner, said patient positioner positioning a treatment portion of a patient within said gap, said flux flowing therethrough, the room space surrounding said gap and said patient positioner extending to the walls comprising an operating space thereabout, said operating space providing operative access to said treatment portion during treatment for a plurality of medical personnel;
   an MRI rf transceiver receiving magnetic resonance imaging data generated from said flux flowing through said treatment portion;
   a computer having a processing unit, said processing unit processing said magnetic resonance imaging data and generating therefrom a plurality of magnetic resonance images on a display device in said magnetic resonance imaging room, said data plurality of magnetic resonance images being dynamically available on said display device and being employed intra-operatively during said treatment of said treatment portion within said room; and
   at least one other medical device within said MRI room space, wherein said at least one other medical device is comprised of an MRI-safe material,
   wherein said MRI room space has an internal height of about 8 feet and an internal width of about 14 feet,
   wherein said processing unit is within said magnetic resonance imaging room,
   wherein at least one covering of said walls, floor and ceiling are formed of non-magnetic material, said material selected from the group consisting of polymeric materials, wood fibers, paper, concrete, plaster, plasterboard, other cementitious materials and combinations thereof, and
   wherein said MRI room space is substantially surrounded by a Faraday shield,
   whereby full access for the treatment of said treatment portion by said plurality of medical personnel from said operating space is provided from substantially all operative angles surrounding said treatment portion, said treatment being aided by dynamic intraoperative magnetic resonance imaging data.

2. The magnetic resonance imaging room according to claim 1, wherein said MRI rf transceiver receives data and said processing unit of said computer processes and displays said plurality of magnetic resonance images in substantially real-time.

3. The magnetic resonance imaging room according to claim 1, wherein said MRI rf transceiver receives said magnetic resonance imaging data and displays said plurality of magnetic resonance images on said display in real-time.

4. A magnetic resonance device comprising:
   a magnetic resonance magnet, magnetic resonance flux lines of said magnet passing through a treatment portion of a patient positioned on a table within an MRI room, said MRI room comprising an operating space surrounding said treatment portion, medical personnel and a surgeon being capable of conducting a treatment on said treatment portion from within said operating space;
   a ferromagnetic shield, said ferromagnetic shield being substantially around said MRI room, preventing outside interference coming into said MRI room and preventing inside interference going outside said MRI room;
   a computer having a processing unit, said processing unit processing dynamic and intra-operative magnetic resonance imaging data from an MRI rf transceiver of said magnetic resonance flux lines flowing through said treatment portion, and generating therefrom a plurality of dynamically available and intraoperative magnetic resonance images;
   a display device, said display device connected to said computer, said display device receiving said plurality of dynamically available and intraoperative magnetic resonance images from said MRI processing unit of said treatment portion of said patient on said table during surgery on said treatment portion; and
   at least one other medical device within said MRI room, wherein said at least one other medical device is comprised of an MRI-safe material,
   wherein said MRI room has an internal height of about 8 feet and an internal width of about 14 feet,
   wherein said processing unit is within said MRI room,
   wherein at least one covering of said MRI room walls, ceiling and floor are formed of non-magnetic material, said material selected from the group consisting of polymeric materials, wood fibers, paper, concrete, plaster, plasterboard, other cementitious materials and combinations thereof, and
   wherein said MRI room is substantially surrounded by a Faraday shield,
   whereby full access for the treatment of said treatment portion from said operating space is provided from substantially all operative angles surrounding said treatment portion, said treatment being aided by dynamic intra-operative magnetic resonance imaging data, and
   whereby said medical personnel and said surgeon using said plurality of dynamic and intraoperative magnetic resonance images guides guide surgery on said patient, and whereby trauma to said patient is minimized.

5. The magnetic resonance device according to claim 4, wherein said display device displays said plurality of dynamically available and intraoperative magnetic resonance images in substantially real-time.

6. The magnetic resonance device according to claim 4, wherein said display device displays said plurality of dynamically available and intraoperative magnetic resonance images in real-time.

7. A magnetic resonance device for guided chemotherapy comprising:
- a magnetic resonance magnet, magnetic resonance flux lines of said magnet passing through a treatment portion of a patient positioned on a table within an MRI room comprising an operating space surrounding said treatment portion, a plurality of health professionals treating said treatment portion from said operating space within said MRI room;
- a ferromagnetic shield, said ferromagnetic shield being substantially around said MRI room, preventing outside interference coming into said MRI room and preventing inside interference going outside said MRI room;
- a computer having a processing unit, said processing unit processing dynamic and intra-operative magnetic resonance imaging data from an MRI rf transceiver of said magnetic resonance flux lines flowing through said treatment portion, and generating therefrom a plurality of dynamically available and intraoperative magnetic resonance images;
- a display device, said display device connected to said computer, said display device receiving said plurality of dynamically available and intraoperative magnetic resonance images of said treatment portion of said patient on said table from said processing unit during treatment on said treatment portion; and
- at least one other medical device within said MRI room, wherein said at least one other medical device is comprised of an MRI-safe material,
- wherein said MRI room has an internal height of about 8 feet and an internal width of about 14 feet,
- wherein said processing unit is within said MRI room,
- wherein at least one covering of said MRI room walls, ceiling and floor are formed of non-magnetic material, said material selected from the group consisting of polymeric materials, wood fibers, paper, concrete, plaster, plasterboard, other cementitious materials and combinations thereof, and
- wherein said MRI room is substantially surrounded by a Faraday shield,
- whereby full access for the treatment of said treatment portion from said operating space is provided to said plurality of health professionals from substantially all operative angles surrounding said treatment portion, said treatment being aided by said dynamic intraoperative magnetic resonance imaging data,
- whereby said plurality of health professionals in said treatment room uses said plurality of dynamic and intraoperative magnetic resonance imaging images to directly guide a needle to a tissue of interest within said treatment portion of said patient, and
- whereby treatment to said treatment portion is targeted and trauma to said patient is minimized.

8. The magnetic resonance device according to claim 7, wherein said display device displays said plurality of dynamically available and intraoperative magnetic resonance images in substantially real-time.

9. The magnetic resonance device according to claim 7, wherein said display device displays said plurality of dynamically available and intraoperative magnetic resonance images in real-time.

10. A magnetic resonance device comprising:
- a magnetic resonance magnet, magnetic resonance flux lines of said magnet passing through a treatment portion of a patient positioned on a table within an MRI room for treatment, medical personnel and a surgeon being capable of conducting treatment on said treatment portion of said patient from an operating space surrounding said treatment portion within said MRI room, said treatment including applying a surgical instrument to a tissue of interest;
- a ferromagnetic shield, said ferromagnetic shield being substantially around said MRI room, preventing outside interference coming into said MRI room and preventing inside interference going outside said MRI room;
- a computer having a processing unit, said processing unit processing dynamic and intra-operative magnetic resonance imaging data from an MRI rf transceiver of said magnetic resonance flux lines flowing through said treatment portion, and generating therefrom a plurality of dynamically available and intraoperative magnetic resonance images;
- a display device, said display device connected to said computer, said display device receiving said plurality of dynamically available and intraoperative magnetic resonance images of a tissue of interest within said treatment portion of said patient on said table; and
- at least one other medical device within said MRI room, wherein said at least one other medical device and said surgical device are comprised of an MRI-safe material,
- wherein said MRI room has an internal height of about 8 feet and an internal width of about 14 feet,
- wherein said processing unit is within said MRI room,
- wherein at least one covering of said MRI room walls, ceiling and floor are formed of non-magnetic material, said material selected from the group consisting of polymeric materials, wood fibers, paper, concrete, plaster, plasterboard, other cementitious materials and combinations thereof, and
- wherein said MRI room is substantially surrounded by a Faraday shield,
- whereby said medical personnel and said surgeon using said dynamically available intraoperative magnetic resonance images minimize trauma to said patient, and
- whereby the extent to which said treatment is maintained throughout a course of therapy can be monitored by said dynamically available intraoperative magnetic resonance images.

11. The magnetic resonance device according to claim 10, wherein said display device displays said plurality of dynamically available and intraoperative magnetic resonance images in substantially real-time.

12. The magnetic resonance device according to claim 10, wherein said display device displays said plurality of dynamically available and intraoperative magnetic resonance images in real-time.

13. A magnetic resonance imaging room comprising:
- a plurality of walls, a floor and a ceiling, defining an MRI room space therein;
- a ferromagnetic shield, said ferromagnetic shield being within said plurality of walls, floor and ceiling to shield said MRI room space from outside interference and prevent outward interference;

a magnet, the poles of said magnet positioned substantially along said floor and ceiling within said MRI room space, said poles having a gap therebetween where lines of flux flow therethrough;

a patient positioner, said patient positioner positioning a treatment portion of patient within said gap, said flux flowing therethrough, the MRI room space surrounding said gap and said patient positioner extending to the walls comprising an operating space thereabout, said operating space providing operative access by medical personnel to said treatment portion during treatment;

an MRI rf transceiver receiving magnetic resonance imaging data generated from said flux flowing through said treatment portion, said data being dynamically available and being employed intra-operatively during said treatment of said treatment portion within said room;

a computer having a processing unit, said processing unit processing said magnetic resonance imaging data and generating therefrom a plurality of magnetic resonance images on a display device in said magnetic resonance imaging room, said plurality of magnetic resonance images being dynamically available on said display device and being employed intra-operatively during a treatment of said treatment portion within said magnetic resonance imaging room;

a surgical instrument for conducting treatment on said treatment portion of said patient within said operating space; and at least one other medical device within said MRI room space, wherein said at least one other medical device and said surgical instrument are comprised of an MRI-safe material, wherein said MRI room space has an internal height of about 8 feet and an internal width of about 14 feet, wherein said processing unit is within said magnetic resonance imaging room, wherein at least one covering of said walls, floor and ceiling are formed of non-magnetic material, said material selected from the group consisting of polymeric materials, wood fibers, paper, concrete, plaster, plasterboard, other cementitious materials and combinations thereof, and wherein said MRI room space is substantially surrounded by a Faraday shield, whereby access for the treatment of said treatment portion by said medical personnel from said operating space is provided from substantially all operative angles surrounding said treatment portion, said treatment being aided by dynamic intraoperative magnetic resonance imaging data.

14. The magnetic resonance imaging room according to claim 13, wherein said display device displays said plurality of dynamically available and intraoperative magnetic resonance images in substantially real-time.

15. The magnetic resonance imaging room according to claim 13, wherein said display device displays said plurality of dynamically available and intraoperative magnetic resonance images in real-time.

16. The magnetic resonance imaging room according to claim 13, wherein said surgical instrument is a catheter.

17. The magnetic resonance imaging room according to claim 16, wherein said catheter is used to deliver a chemotherapeutic agent to a tumor.

18. The magnetic resonance imaging room according to claim 16, wherein said catheter is used to deliver a therapeutic agent to a tumor.

19. The magnetic resonance imaging room according to claim 16, wherein said catheter is used to deliver a therapeutic chemical to a tumor.

20. The magnetic resonance imaging room according to claim 16, wherein said catheter is used to deliver a magnetic tag to a tissue of interest.

21. The magnetic resonance imaging room according to claim 16, wherein said catheter is used to conduct a biopsy on a tissue of interest.

22. The magnetic resonance imaging room according to claim 16, wherein said catheter is used to place an indwelling catheter in said patient.

23. The magnetic resonance imaging room according to claim 13, wherein said surgical instrument is a flexible endoscope.

24. A method of conducting treatment in a magnetic resonance imaging treatment room, said method comprising the steps of:

positioning a treatment portion of a patient in said MRI treatment room, the room having a magnet, the poles of said magnet positioned substantially along a floor and ceiling within said MRI treatment room, said poles having a gap therebetween where lines of flux flow therethrough, receiving, by an MRI rf transceiver receiving magnetic resonance imaging data generated from flux flowing through said treatment portion;

processing, by a processing unit, said magnetic resonance imaging data and generating therefrom a plurality of magnetic resonance images on a display in said MRI treatment room, said data plurality of magnetic resonance images being dynamically available and being employed intra-operatively during treatment of said treatment portion within said MRI treatment room, the room space surrounding said gap and said patient extending to the walls comprising an operating space thereabout, said operating space providing operative access to said treatment portion during treatment, a ferromagnetic shield, said ferromagnetic shield being substantially around said MRI treatment room to shield said MRI treatment room from outside interference and prevent outward interference; and conducting a treatment upon said treatment portion of said patient in said MRI treatment room employing said plurality of magnetic resonance images on said display, said treatment including employment of another medical device on said patient during said treatment of said treatment portion, wherein said another medical device is comprised of an MRI-safe material, said MRI rf transceiver gathering magnetic resonance imaging data about said treatment portion and the effect of said treatment on said treatment portion, wherein said magnetic resonance imaging treatment room has an internal height of about 8 feet and an internal width of about 14 feet, wherein said processing unit is within said magnetic resonance imaging treatment room, wherein at least one covering of said MRI treatment room walls, ceiling and floor are formed of non-magnetic material, said material selected from the group consisting of polymeric materials, wood fibers, paper, concrete, plaster, plasterboard, other cementitious materials and combinations thereof, and wherein said MRI treatment room is substantially surrounded by a Faraday shield, whereby access for the treatment of said treatment portion from said operating space is provided from substantially all operative angles surrounding said treatment portion, said treatment being aided by dynamic intraoperative magnetic resonance imaging data.

25. The magnetic resonance imaging room according to claim 1, wherein said display device receives dynamically available and intraoperative magnetic resonance imaging of said treatment portion of said patient on said patient positioner during said treatment on said treatment portion,
   whereby dynamic and intraoperative magnetic resonance imaging guides said treatment on said patient, and
   whereby trauma to said patient is minimized.

26. The magnetic resonance imaging room according to claim 1, wherein said display device receives dynamically available and intraoperative magnetic resonance imaging of said treatment portion of said patient on said patient positioner during said treatment on said treatment portion,
   whereby a health professional in said MRI room uses said dynamic and intraoperative magnetic resonance imaging to directly guide a needle to a tissue of interest within said treatment portion of said patient, and
   whereby treatment to said treatment portion is targeted and trauma to said patient is minimized.

27. The magnetic resonance imaging room according to claim 1, wherein at least one of said plurality of walls is angular.

28. The magnetic resonance imaging room according to claim 27, wherein said plurality of walls comprise a circle, said MRI room being circular.

29. The magnetic resonance imaging room according to claim 1, wherein at least one of said plurality of walls, floor and ceiling comprise a false wall.

30. The magnetic resonance imaging room according to claim 1, further comprising:
   a magnetic shield, said magnetic shield containing said flux flow within said MRI room.

31. The magnetic resonance imaging room according to claim 30, wherein said MRI room is one of a plurality of rooms in a building, said magnetic shield isolating said MRI room within said building.

32. The magnetic resonance imaging room according to claim 30, wherein said magnetic shield is active.

33. The magnetic resonance imaging room according to claim 30, wherein said magnetic shield is passive.

34. The magnetic resonance imaging room according to claim 1, further comprising a Faraday shield.

35. The magnetic resonance imaging room according to claim 1, further comprising at least one bucking flux element.

36. The magnetic resonance imaging room according to claim 1, further comprising at least one blocking element.

37. The magnetic resonance imaging room according to claim 1, wherein said patient positioner positions said treatment portion of said patient about the X, Y and Z axes and combinations thereof.

38. The magnetic resonance imaging room according to claim 1, wherein an interior surface of at least one of said plurality of walls, floor, ceiling and magnet are covered with a pictorial.

39. The magnetic resonance imaging room according to claim 1, wherein said magnetic resonance imaging room comprises an operating room.

40. The magnetic resonance imaging room according to claim 1, wherein said magnet has a strength between 0.1-3.0 Tesla.

41. The magnetic resonance imaging room according to claim 40, wherein said magnet strength is between 0.5-1.5 Tesla.

42. The magnetic resonance imaging room according to claim 1, wherein said magnet has a strength over 3.0 Tesla.

43. The magnetic resonance imaging room according to claim 1, wherein said magnet is positioned sideways and substantially vertically on said floor along a horizontal axis within said MRI room space, the poles of said magnet being aligned substantially perpendicular to said floor and having said gap therebetween with lines of flux flowing therethrough, said lines of flux being substantially horizontal and parallel to the planes of said floor and ceiling.

44. The magnetic resonance imaging room according to claim 43, wherein at least one pole of said magnet is covered by a false wall.

45. The magnetic resonance imaging room according to claim 1, wherein the poles of said magnet are arranged asymmetrically in relation to said floor and ceiling.

46. A magnetic resonance imaging room comprising:
   a plurality of walls, a floor and a ceiling, defining an MRI room space therein;
   a ferromagnetic shield, said ferromagnetic shield being within said plurality of walls, floor and ceiling to shield said MRI room space from outside interference and prevent outward interference;
   a magnet, the poles of said magnet positioned substantially along said floor and ceiling within said MRI room space, said poles having a gap therebetween where lines of flux flow therethrough;
   an adjustable patient bed, said bed facilitating access to a treatment portion of a patient within said gap, said flux flowing therethrough, the room space surrounding said gap and said patient bed extending to the walls comprising an operating space thereabout, said operating space providing operative access to said treatment portion during treatment by medical personnel;
   an MRI receiver, said MRI receiver receiving magnetic resonance imaging data generated from said flux flowing through said treatment portion,
   a computer having a processing unit, said processing unit processing said magnetic resonance imaging data and generating therefrom a plurality of magnetic resonance images on a display device in said magnetic resonance imaging room, said data plurality of magnetic resonance images being dynamically available on said display device and being employed intra-operatively during said treatment of said treatment portion within said room; and
   at least one other medical device within said MRI room space, wherein said at least one other medical device is comprised of an MRI-safe material,
   wherein said magnetic resonance imaging room has an internal height of about 8 feet and an internal width of about 14 feet,
   wherein said processing unit is within said magnetic resonance imaging room,
   wherein at least one covering of said walls, floor and ceiling are formed of non-magnetic material, said material selected from the group consisting of polymeric materials, wood fibers, paper, concrete, plaster, plasterboard, other cementitious materials and combinations thereof, and
   wherein said MRI room space is substantially surrounded by a Faraday shield,
   whereby access for the treatment of said treatment portion by said medical personnel from said operating space is provided from substantially all operative angles surrounding treatment portion, said treatment being aided by dynamic intraoperative magnetic resonance imaging data.

47. A magnetic resonance imaging room comprising:

a plurality of walls, a floor and a ceiling, defining an MRI room space therein;

a ferromagnetic shield, said ferromagnetic shield being within said plurality of walls, floor and ceiling to shield said MRI room space from outside interference and prevent outward interference;

a magnet, the poles of said magnet positioned substantially along said floor and ceiling within said MRI room space, said poles having a gap therebetween where lines of flux flow therethrough;

an adjustable patient bed, said bed facilitating access to a treatment portion of a patient within said gap, said flux flowing therethrough, the room space surrounding said gap and said patient bed extending to the walls comprising an operating space thereabout, said operating space providing operative access to said treatment portion during treatment;

an MRI receiver, said MRI receiver receiving magnetic resonance imaging data generated from said flux flowing through said treatment portion, a computer having a processing unit, said processing unit processing said magnetic resonance imaging data and generating therefrom a plurality of magnetic resonance images on a display device in said magnetic resonance imaging room, said data plurality of magnetic resonance images being dynamically available on said display device and being employed intra-operatively during said treatment of said treatment portion within said room;

a surgical instrument for conducting treatment on said treatment portion of said patient within said operating space; and at least one other medical device within said MRI room space, wherein said at least one other medical device and said surgical instrument are comprised of an MRI-safe material, wherein said magnetic resonance imaging room has an internal height of about 8 feet and an internal width of about 14 feet, wherein said processing unit is within said magnetic resonance imaging room, wherein at least one covering of said walls, floor and ceiling are formed of non-magnetic material, said material selected from the group consisting of polymeric materials, wood fibers, paper, concrete, plaster, plasterboard, other cementitious materials and combinations thereof, and wherein said MRI room space is substantially surrounded by a Faraday shield, whereby access for the treatment of said treatment portion by medical personnel from said operating space is provided from substantially all operative angles sounding said treatment portion, said treatment being aided by dynamic intraoperative magnetic resonance imaging data.

48. A magnetic resonance imaging room comprising:

a plurality of walls, a floor and a ceiling, defining an MRI room space therein;

a ferromagnetic shield, said ferromagnetic shield being within said plurality of walls, floor and ceiling to shield said MRI room space from outside interference and prevent outward interference;

a magnet, the poles of said magnet positioned substantially along said floor and ceiling within said MRI room space, said poles having a gap therebetween where lines of flux flow therethrough, a treatment portion of a patient being placed within said gap, said flux flowing therethrough;

an MRI rf transceiver receiving magnetic resonance imaging data generated from said flux flowing through said treatment portion, a computer having a processing unit, said processing unit processing said magnetic resonance imaging data and generating therefrom a plurality of magnetic resonance images on a display device in said magnetic resonance imaging room, said data plurality of magnetic resonance images being dynamically available on said display device and being employed intra-operatively during a treatment of said treatment portion within said MRI room; and at least one other medical device within said MRI room space, wherein said at least one other medical device is comprised of an MRI-safe material, wherein said magnetic resonance imaging room has an internal height of about 8 feet and an internal width of about 14 feet, wherein said processing unit is within said magnetic resonance imaging room, wherein at least one covering of said walls, floor and ceiling are formed of non-magnetic material, said material selected from the group consisting of polymeric materials, wood fibers, paper, concrete, plaster, plasterboard, other cementitious materials and combinations thereof, and wherein said MRI room space is substantially surrounded by a Faraday shield, whereby full access for the treatment of said treatment portion by medical personnel from said operating space is provided from substantially all operative angles surrounding said treatment portion, said treatment being aided by dynamic intraoperative magnetic resonance imaging data.

* * * * *